United States Patent
Liu et al.

(10) Patent No.: US 8,633,235 B2
(45) Date of Patent: *Jan. 21, 2014

(54) BENZIMIDAZOLE DERIVATIVES, COMPOSITIONS CONTAINING THEM, PREPARATION THEREOF AND USES THEREOF

(75) Inventors: Ziping Liu, Québec (CA); Daniel Pagé, Québec (CA); Christopher Walpole, Québec (CA); Hua Yang, Québec (CA)

(73) Assignee: Neomed Institute, Montreal, Quebec (CA)

( * ) Notice: Subject to any disclaimer, the term of this patent is extended or adjusted under 35 U.S.C. 154(b) by 1345 days.

This patent is subject to a terminal disclaimer.

(21) Appl. No.: 10/573,054

(22) PCT Filed: Sep. 24, 2004

(86) PCT No.: PCT/GB2004/004124

§ 371 (c)(1), (2), (4) Date: Mar. 11, 2008

(87) PCT Pub. No.: WO2005/030732

PCT Pub. Date: Apr. 7, 2005

(65) Prior Publication Data

US 2008/0207612 A1 Aug. 28, 2008

(30) Foreign Application Priority Data

Sep. 26, 2003 (SE) .................. 0302573

(51) Int. Cl.
*A61K 31/4184* (2006.01)
*C07D 235/04* (2006.01)

(52) U.S. Cl.
USPC ............ 514/394; 548/302.7; 548/304.4; 548/309.7; 514/385

(58) Field of Classification Search
USPC .............. 548/302.7, 304.4, 310.7, 309.7; 514/385, 387, 394
See application file for complete search history.

(56) References Cited

U.S. PATENT DOCUMENTS

| | | | |
|---|---|---|---|
| 5,482,956 A | 1/1996 | Lunkenheimer et al. | |
| 6,166,219 A | 12/2000 | Yamasaki et al. | |
| 6,348,032 B1 | 2/2002 | Sperl et al. | |
| 6,352,985 B1 | 3/2002 | Yamasaki et al. | |
| 6,376,515 B2 | 4/2002 | Zhu et al. | |
| 6,534,535 B1 | 3/2003 | Zhu et al. | |
| 6,632,815 B2 | 10/2003 | Zhu et al. | |
| 6,686,368 B1 | 2/2004 | Zhu et al. | |
| 6,720,317 B1 | 4/2004 | Zhu et al. | |
| 6,835,739 B2 | 12/2004 | Zhu et al. | |
| 6,844,367 B1 | 1/2005 | Zhu et al. | |
| 7,329,679 B2 * | 2/2008 | Halfbrodt et al. | 514/357 |
| 7,345,075 B2 * | 3/2008 | Halfbrodt et al. | 514/394 |
| 7,501,447 B2 * | 3/2009 | Liu et al. | 514/394 |
| 7,517,898 B2 * | 4/2009 | Liu et al. | 514/394 |
| 7,550,495 B2 * | 6/2009 | Page et al. | 514/394 |
| 7,615,642 B2 * | 11/2009 | Brown et al. | 548/304.7 |
| 2002/0006948 A1 | 1/2002 | Halfbrodt et al. | |
| 2002/0082280 A1 | 6/2002 | Sperl et al. | |
| 2004/0116465 A1 | 6/2004 | Cheng et al. | |
| 2006/0052421 A1 | 3/2006 | Welter et al. | |
| 2006/0094750 A1 | 5/2006 | Kon-I et al. | |
| 2007/0225346 A1 | 9/2007 | Bohlin et al. | |
| 2007/0244092 A1 | 10/2007 | Brown et al. | |
| 2010/0305140 A1 | 12/2010 | Brown et al. | |

FOREIGN PATENT DOCUMENTS

| | | |
|---|---|---|
| EP | 0597304 | 5/1994 |
| EP | 0583665 B1 | 3/2003 |
| EP | 1403255 A1 | 3/2004 |
| FR | 5354 M | 9/1967 |
| FR | 1604908 | 6/1972 |
| WO | 9411349 | 5/1994 |
| WO | 9411350 | 5/1994 |
| WO | 9724334 A1 | 7/1997 |
| WO | 0112600 A1 | 2/2001 |
| WO | 0119798 A2 | 3/2001 |
| WO | 0151473 | 7/2001 |

(Continued)

OTHER PUBLICATIONS

Kuhnke et al (2001): STN International HCAPLUS database, (Columbus, Ohio), Accession No. 2001:526062.*
Final Rejection issued for U.S. Appl. No. 11/419,603 on Dec. 24, 2008.
Final Rejection issued for U.S. Appl. No. 11/689,864 on Jan. 8, 2009.
Chawla et al., "Challenges in Polymorphism of Pharmaceuticals," CRIPS, vol. 5(1), Jan.-Mar. 2004, pp. 9-12.
Newman et al., "Solid-state analysis of the active pharmaceutical ingredient in drug products," Drug Discovery Today, vol. 8(19), Oct. 2003, pp. 898-905.
Li et al., "Benzimidazole derivatives as novel nonpeptide luteinizing hormone-releasing hormone (LHRH) antagonists. Part 2: Benzimidazole-5-sulfonamides," Bioorganic & Medicinal Chemistry Letters, 2005, 15(3), pp. 805-807.
STN Intnl, file REGISTRY, see RN: 848855-83-4.
STN Intnl, File CAPLUS, accession No. 1975:408737, doc No. 83:8737, Bieksa, V. et al., "Relation of the reactivity of chloroethyl derivatives of 3,4-diaminobenzenesulfopiperidides to the structure of alkylating group", Lietuvos TSR Mokslu Akademijos Darbai, Serija B: Chemija, Technika, Fizine Geografija, (1974), (3) 91-8.

(Continued)

Primary Examiner — Golam M Shameem
(74) Attorney, Agent, or Firm — Choate, Hall & Stewart, LLP; Charles E. Lyon; Xiaodong Li

(57) ABSTRACT

Compounds of Formula (I) or pharmaceutically acceptable salts thereof; wherein $R^1$, $R^2$, $R^3$, and $R^4$ are as defined in the specification as well as salts and pharmaceutical compositions including the compounds are prepared. They are useful in therapy, in particular in the management of pain.

I

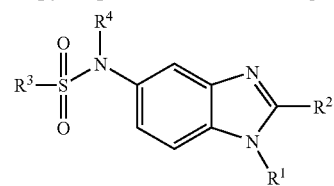

4 Claims, No Drawings

(56) References Cited

FOREIGN PATENT DOCUMENTS

| WO | 0200651 | A2 | 1/2002 |
|---|---|---|---|
| WO | 0246168 | A1 | 6/2002 |
| WO | 02085866 | | 10/2002 |
| WO | 2004085385 | A2 | 10/2004 |
| WO | 2004108688 | A1 | 12/2004 |
| WO | 2004108712 | | 12/2004 |
| WO | 2005007625 | A2 | 1/2005 |
| WO | 2005021547 | | 3/2005 |
| WO | 2005030732 | A1 | 4/2005 |
| WO | 2005030733 | | 4/2005 |
| WO | 2005030761 | | 4/2005 |
| WO | 2005030762 | | 4/2005 |
| WO | 2005113542 | A2 | 12/2005 |
| WO | 2006009876 | A2 | 1/2006 |
| WO | 2006012642 | A2 | 2/2006 |
| WO | 2006033627 | | 3/2006 |
| WO | 2006033628 | | 3/2006 |
| WO | 2006033629 | | 3/2006 |
| WO | 2006033630 | | 3/2006 |
| WO | 2006033631 | | 3/2006 |
| WO | 2006033632 | | 3/2006 |
| WO | 2006033633 | | 3/2006 |
| WO | 2006048754 | A1 | 5/2006 |
| WO | 2006078941 | A2 | 7/2006 |
| WO | 2007108754 | A1 | 9/2007 |
| WO | 2007120101 | A1 | 10/2007 |

OTHER PUBLICATIONS

STN Intnl, File CAPLUS, accession No. 1973:515496, doc No. 79:115496, Bieksa, V. et al. "Chloroalkyl derivatives of benzimidazoles. 1. Chloroethyl derivatives of 2-methylbenzimidazole-5-sulfonamide," Lietuvos TSR Mokslu Akademijos Darbai, Serija B: Chemija, Technika, Fizine Geografija, (1973), (2), 93-103.

English abstract for WO 9724334.

Non-Final Office Action issued for U.S. Appl. No. 11/419,603 on Dec. 12, 2007.

Notice of Allowance issued for U.S. Appl. No. 11/419,603 on Mar. 10, 2009.

Interview Summary issued for U.S. Appl. No. 11/419,603 on Mar. 18, 2008.

Restriction Requirement issued for U.S. Appl. No. 11/689,864 on Mar. 24, 2008.

Notice of Allowance issued for U.S. Appl. No. 11/689,864 on Apr. 10, 2009.

Evans et al., "Synthesis of a group of 1H-benzimidazoles and their screening for antiinflammatory activity," Eur J Med Chem, 1996, vol. 31, pp. 635-642, example 27.

Holenz et al., "Medicinal chemistry driven approaches toward novel and selective serotonin 5-HT6 receptor ligands," J. Med. Chem., 2005, vol. 48, pp. 1781-1795, table 1, compound 16, abstract.

STN International, File CAPLUS, accession No. 1972:419030, doc. No. 77:19030, Koshienko et al., "Benzo(1,2-d:3,4-d')diimidazole derivatives. II. Behavior of 3,6-dimethyl-and 3,6,7-trimethylbenzo(1,2-d:3,4-d')diimidazole toward nucleophilic agents," Khimiya Geterotsiklicheskikh Soedinenii, 1971, 7(8), pp. 1132-1135; XP002307925.

STN Intnl, File CHEMCATS, access No. 2003:1839419, "Benzenesulfonamide, N-(1,2-dimethyl-1H-benzimidazol-5-yl)-", CAS Reg No. 488708-12-9; & STN Intnl, File CHEMCATS, access No. 2003:2399372, "Benzenesulfonamide, N-(2-methyl-1-(phenylmethyl)-1H-benzimidazol-5-yl-", CAS Registry No. 488841-64-1; & STN Intnl, File CHEMCATS, access No. 2003:2595844, "Benzenesulfonamide, 4-methyl-N-(2-methyl-1-(phenylmethyl)-1H-benzimidazole-5-yl)-", CAS Reg No. 312617-94-0.

STN Intnl, File CHEMCATS, accession No. 2003:1839419, "Benzenesulfonamide, N-(1,2-dimethyl-1H-benzimidazol-5-yl)-" CAS Registry No. 488708-12-9; & STN Intnl, File CHEMCATS, accession No. 2003:1845322, "Benzenesulfonamide, 4-bromo-N-(1,2-dimethyl-1H-benzimidazol-5-yl)-", CAS Registry No. 489397-82-2; & STN Intnl. File CHEMCATS, accession No. 2003:2305521, "Benzenesulfonamide, N-(1,2-dimethyl-1H-benzimidazol-5-yl)-1-fluoro-", CAS Registry No. 503429-33-2.

Brittain et al., "Effects of Pharmaceutical Processing on Drug Polymorphs and Solvates," Polymorphism in Pharmaceutical Solids, vol. 95, pp. 331-361.

Non-Final Office Action issued for U.S. Appl. No. 11/419,603 on Jun. 23, 2008.

Non-Final Office Action issued for U.S. Appl. No. 11/689,864 on Jul. 9, 2008.

Express-Pharma-Online (http://www.expresspharmaonline.com/20031023/edit02.shtml).

* cited by examiner

BENZIMIDAZOLE DERIVATIVES, COMPOSITIONS CONTAINING THEM, PREPARATION THEREOF AND USES THEREOF

CROSS-REFERENCE TO RELATED APPLICATIONS

This application is a US National Stage under 35 U.S.C §371 of International Application No. PCT/GB2004/004124, filed on Sep. 24, 2004, which claims priority under 35 U.S.C. §119(a)-(d) to Swedish Application No. 0302573-1, filed on Sep. 26, 2003.

BACKGROUND OF THE INVENTION

1. Field of the Invention

The invention is related to therapeutic compounds, pharmaceutical compositions containing these compounds, manufacturing processes thereof and uses thereof. Particularly, the present invention is related to compounds that may be effective in treating pain, cancer, multiple sclerosis, Parkinson's disease, Huntington's chorea, Alzheimer's disease, anxiety disorders, gastrointestinal disorders and/or cardiovascular disorders.

2. Discussion of Relevant Technology

Pain management has been an important field of study for many years. It has been well known that cannabinoid receptor (e.g., $CB_1$ receptor, $CB_2$ receptor) ligands including agonists, antagonists and inverse agonists produce relief of pain in a variety of animal models by interacting with $CB_1$ and/or $CB_2$ receptors. Generally, $CB_1$ receptors are located predominately in the central nervous system, whereas $CB_2$ receptors are located primarily in the periphery and are primarily restricted to the cells and tissues derived from the immune system.

While $CB_1$ receptor agonists, such as $\Delta^9$-tetrahydrocannabinol ($\Delta^9$-THC) and anadamide, are useful in anti-nociception models in animals, they tend to exert undesired CNS side-effects, e.g., psychoactive side effects, the abuse potential, drug dependence and tolerance, etc. These undesired side effects are known to be mediated by the $CB_1$ receptors located in CNS. There are lines of evidence, however, suggesting that $CB_1$ agonists acting at peripheral sites or with limited CNS exposure can manage pain in humans or animals with much improved overall in vivo profile.

Therefore, there is a need for new $CB_1$ receptor ligands such as agonists that may be useful in managing pain or treating other related symptoms or diseases with reduced or minimal undesirable CNS side-effects.

DESCRIPTION OF THE EMBODIMENTS

The present invention provides $CB_1$ receptor ligands which may be useful in treating pain and/or other related symptoms or diseases.

Unless specified otherwise within this specification, the nomenclature used in this specification generally follows the examples and rules stated in *Nomenclature of Organic Chemistry, Sections A, B, C, D, E, F, and H*, Pergamon Press, Oxford, 1979, which is incorporated by references herein for its exemplary chemical structure names and rules on naming chemical structures.

"$CB_1/CB_2$ receptors" means $CB_1$ and/or $CB_2$ receptors.

The term "$C_{m-n}$" or "$C_{m-n}$ group" used alone or as a prefix, refers to any group having m to n carbon atoms.

The term "hydrocarbon" used alone or as a suffix or prefix, refers to any structure comprising only carbon and hydrogen atoms up to 14 carbon atoms. The term "hydrocarbon radical" or "hydrocarbyl" used alone or as a suffix or prefix, refers to any structure as a result of removing one or more hydrogens from a hydrocarbon.

The term "alkyl" used alone or as a suffix or prefix, refers to monovalent straight or branched chain hydrocarbon radicals comprising 1 to about 12 carbon atoms. Unless otherwise specified, "alkyl" general includes both saturated alkyl and unsaturated alkyl.

The term "alkylene" used alone or as a suffix or prefix, refers to divalent straight or branched chain hydrocarbon radicals comprising 1 to about 12 carbon atoms, which serves to links two structures together.

The term "alkenyl" used alone or as a suffix or prefix, refers to a monovalent straight or branched chain hydrocarbon radical having at least one carbon-carbon double bond and comprising at least 2 up to about 12 carbon atoms.

The term "alkynyl" used alone or as a suffix or prefix, refers to a monovalent straight or branched chain hydrocarbon radical having at least one carbon-carbon triple bond and comprising at least 2 up to about 12 carbon atoms.

The term "cycloalkyl," used alone or as a suffix or prefix, refers to a monovalent ring-containing hydrocarbon radical comprising at least 3 up to about 12 carbon atoms. "Cycloalkyl" includes both monocyclic and multicyclic hydrocarbon structures. Multicyclic hydrocarbon structure includes non-fused, fused and bridged rings.

The term "cycloalkenyl" used alone or as a suffix or prefix, refers to a monovalent ring-containing hydrocarbon radical having at least one carbon-carbon double bond and comprising at least 3 up to about 12 carbon atoms. "Cycloalkenyl" includes both monocyclic and multicyclic hydrocarbon structures. Multicyclic hydrocarbon structure includes non-fused, fused and bridged rings.

The term "cycloalkynyl" used alone or as a suffix or prefix, refers to a monovalent ring-containing hydrocarbon radical having at least one carbon-carbon triple bond and comprising about 7 up to about 12 carbon atoms.

The term "aryl" used alone or as a suffix or prefix, refers to a hydrocarbon radical having one or more polyunsaturated carbon rings having aromatic character, (e.g., 4n+2 delocalized electrons) and comprising 5 up to about 14 carbon atoms, wherein the radical is located on a carbon of the aromatic ring.

The term "non-aromatic group" or "non-aromatic" used alone, as a suffix or as prefix, refers to a chemical group or radical that does not contain a ring having aromatic character (e.g., 4n+2 delocalized electrons).

The term "arylene" used alone or as a suffix or prefix, refers to a divalent hydrocarbon radical having one or more polyunsaturated carbon rings having aromatic character, (e.g., 4n+2 delocalized electrons) and comprising 5 up to about 14 carbon atoms, which serves to link two structures together.

The term "heterocycle" used alone or as a suffix or prefix, refers to a ring-containing structure or molecule having one or more multivalent heteroatoms, independently selected from N, O, P and S, as a part of the ring structure and including at least 3 and up to about 20 atoms in the ring(s). Heterocycle may be saturated or unsaturated, containing one or more double bonds, and heterocycle may contain more than one ring. When a heterocycle contains more than one ring, the rings may be fused or unfused. Fused rings generally refer to at least two rings share two atoms therebetween. Heterocycle may have aromatic character or may not have aromatic character.

The term "heteroalkyl" used alone or as a suffix or prefix, refers to a radical formed as a result of replacing one or more carbon atom of an alkyl with one or more heteroatoms selected from N, O, P and S.

The term "heteroaromatic" used alone or as a suffix or prefix, refers to a ring-containing structure or molecule having one or more multivalent heteroatoms, independently selected from N, O, P and S, as a part of the ring structure and including at least 3 and up to about 20 atoms in the ring(s), wherein the ring-containing structure or molecule has an aromatic character (e.g., 4n+2 delocalized electrons).

The term "heterocyclic group," "heterocyclic moiety," "heterocyclic," or "heterocyclo" used alone or as a suffix or prefix, refers to a radical derived from a heterocycle by removing one or more hydrogens therefrom.

The term "heterocyclyl" used alone or as a suffix or prefix, refers a radical derived from a heterocycle by removing at least one hydrogen from a carbon of a ring of the heterocycle.

The term "heterocyclylene" used alone or as a suffix or prefix, refers to a divalent radical derived from a heterocycle by removing two hydrogens therefrom, which serves to link two structures together.

The term "heteroaryl" used alone or as a suffix or prefix, refers to a heterocyclyl having aromatic character, wherein the radical of the heterocyclyl is located on a carbon of an aromatic ring of the heterocyclyl. A heteroaryl may contain both aromatic and non-aromatic rings therein. These rings may be fused or otherwised linked together.

The term "heterocycloalkyl" used alone or as a suffix or prefix, refers to a heterocyclyl that does not have aromatic character.

The term "heteroarylene" used alone or as a suffix or prefix, refers to a heterocyclylene having aromatic character.

The term "heterocycloalkylene" used alone or as a suffix or prefix, refers to a heterocyclylene that does not have aromatic character.

The term "six-membered" used as a prefix refers to a group having a ring that contains six ring atoms.

The term "five-membered" used as a prefix refers to a group having a ring that contains five ring atoms.

A five-membered ring heteroaryl is a heteroaryl with a ring having five ring atoms wherein 1, 2 or 3 ring atoms are independently selected from N, O and S.

Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl.

A six-membered ring heteroaryl is a heteroaryl with a ring having six ring atoms wherein 1, 2 or 3 ring atoms are independently selected from N, O and S.

Exemplary six-membered ring heteroaryls are pyridyl, pyrazinyl, pyrimidinyl, triazinyl and pyridazinyl.

The term "substituted" used as a prefix refers to a structure, molecule or group, wherein one or more hydrogens are replaced with one or more $C_{1-12}$hydrocarbon groups, or one or more chemical groups containing one or more heteroatoms selected from N, O, S, F, Cl, Br, I, and P. Exemplary chemical groups containing one or more heteroatoms include heterocyclyl, —$NO_2$, —OR, —Cl, —Br, —I, —F, —$CF_3$, —C(=O)R, —C(=O)OH, —$NH_2$, —SH, —NHR, —$NR_2$, —SR, —$SO_3H$, —$SO_2R$, —S(=O)R, —CN, —OH, —C(=O)OR, —C(=O)$NR_2$, —NRC(=O)R, oxo (=O), imino (=NR), thio and oximino (=N—OR), wherein each "R" is a $C_{1-12}$hydrocarbyl. For example, substituted phenyl may refer to nitrophenyl, pyridylphenyl, methoxyphenyl, chlorophenyl, aminophenyl, etc., wherein the nitro, pyridyl, methoxy, chloro, and amino groups may replace any suitable hydrogen on the phenyl ring.

The term "substituted" used as a suffix of a first structure, molecule or group, followed by one or more names of chemical groups refers to a second structure, molecule or group, which is a result of replacing one or more hydrogens of the first structure, molecule or group with the one or more named chemical groups. For example, a "phenyl substituted by nitro" refers to nitrophenyl.

The term "optionally substituted" refers to both groups, structures, or molecules that are substituted and those that are not substituted.

Heterocycle includes, for example, monocyclic heterocycles such as: aziridine, oxirane, thiirane, azetidine, oxetane, thietane, pyrrolidine, pyrroline, imidazolidine, pyrazolidine, pyrazoline, dioxolane, sulfolane 2,3-dihydrofuran, 2,5-dihydrofuran tetrahydrofuran, thiophane, piperidine, 1,2,3,6-tetrahydro-pyridine, piperazine, morpholine, thiomorpholine, pyran, thiopyran, 2,3-dihydropyran, tetrahydropyran, 1,4-dihydropyridine, 1,4-dioxane, 1,3-dioxane, dioxane, homopiperidine, 2,3,4,7-tetrahydro-1H-azepine homopiperazine, 1,3-dioxepane, 4,7-dihydro-1,3-dioxepin, and hexamethylene oxide.

In addition, heterocycle includes aromatic heterocycles, for example, pyridine, pyrazine, pyrimidine, pyridazine, thiophene, furan, furazan, pyrrole, imidazole, thiazole, oxazole, pyrazole, isothiazole, isoxazole, 1,2,3-triazole, tetrazole, 1,2,3-thiadiazole, 1,2,3-oxadiazole, 1,2,4-thiadiazole, 1,2,4-oxadiazole, 1,3,4-triazole, 1,3,4-thiadiazole, and 1,3,4-oxadiazole.

Additionally, heterocycle encompass polycyclic heterocycles, for example, indole, indoline, isoindoline, quinoline, tetrahydroquinoline, isoquinoline, tetrahydroisoquinoline, 1,4-benzodioxan, coumarin, dihydrocoumarin, benzofuran, 2,3-dihydrobenzofuran, isobenzofuran, chromene, chroman, isochroman, xanthene, phenoxathiin, thianthrene, indolizine, isoindole, indazole, purine, phthalazine, naphthyridine, quinoxaline, quinazoline, cinnoline, pteridine, phenanthridine, perimidine, phenanthroline, phenazine, phenothiazine, phenoxazine, 1,2-benzisoxazole, benzothiophene, benzoxazole, benzthiazole, benzimidazole, benztriazole, thioxanthine, carbazole, carboline, acridine, pyrolizidine, and quinolizidine.

In addition to the polycyclic heterocycles described above, heterocycle includes polycyclic heterocycles wherein the ring fusion between two or more rings includes more than one bond common to both rings and more than two atoms common to both rings. Examples of such bridged heterocycles include quinuclidine, diazabicyclo[2.2.1]heptane and 7-oxabicyclo[2.2.1]heptane.

Heterocyclyl includes, for example, monocyclic heterocyclyls, such as: aziridinyl, oxiranyl, thiiranyl, azetidinyl, oxetanyl, thietanyl, pyrrolidinyl, pyrrolinyl, imidazolidinyl, pyrazolidinyl, pyrazolinyl, dioxolanyl, sulfolanyl, 2,3-dihydrofuranyl, 2,5-dihydrofuranyl, tetrahydrofuranyl, thiophanyl, piperidinyl, 1,2,3,6-tetrahydro-pyridinyl, piperazinyl, morpholinyl, thiomorpholinyl, pyranyl, thiopyranyl, 2,3-dihydropyranyl, tetrahydropyranyl, 1,4-dihydropyridinyl, 1,4-dioxanyl, 1,3-dioxanyl, dioxanyl, homopiperidinyl, 2,3,4,7-tetrahydro-1H-azepinyl, homopiperazinyl, 1,3-dioxepanyl, 4,7-dihydro-1,3-dioxepinyl, and hexamethylene oxidyl.

In addition, heterocyclyl includes aromatic heterocyclyls or heteroaryl, for example, pyridinyl, pyrazinyl, pyrimidinyl, pyridazinyl, thienyl, furyl, furazanyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4 oxadiazolyl.

Additionally, heterocyclyl encompasses polycyclic heterocyclyls (including both aromatic or non-aromatic), for example, indolyl, indolinyl, isoindolinyl, quinolinyl, tetrahydroquinolinyl, isoquinolinyl, tetrahydroisoquinolinyl, 1,4-benzodioxanyl, coumarinyl, dihydrocoumarinyl, benzofuranyl, 2,3-dihydrobenzofuranyl, isobenzofuranyl, chromenyl, chromanyl, isochromanyl, xanthenyl, phenoxathiinyl, thianthrenyl, indolizinyl, isoindolyl, indazolyl, purinyl, phthalazinyl, naphthyridinyl, quinoxalinyl, quinazolinyl, cinnolinyl, pteridinyl, phenanthridinyl, perimidinyl, phenanthrolinyl, phenazinyl, phenothiazinyl, phenoxazinyl, 1,2-benzisoxazolyl, benzothiophenyl, benzoxazolyl, benzthiazolyl, benzimidazolyl, benztriazolyl, thioxanthinyl, carbazolyl, carbolinyl, acridinyl, pyrolizidinyl, and quinolizidinyl.

In addition to the polycyclic heterocyclyls described above, heterocyclyl includes polycyclic heterocyclyls wherein the ring fusion between two or more rings includes more than one bond common to both rings and more than two atoms common to both rings. Examples of such bridged heterocyclyls include quinuclidinyl, diazabicyclo[2.2.1]heptyl; and 7-oxabicyclo[2.2.1]heptyl.

The term "alkoxy" used alone or as a suffix or prefix, refers to radicals of the general formula —O—R, wherein —R is selected from a hydrocarbon radical. Exemplary alkoxy includes methoxy, ethoxy, propoxy, isopropoxy, butoxy, t-butoxy, isobutoxy, cyclopropylmethoxy, allyloxy, and propargyloxy.

The term "aryloxy" used alone or as a suffix or prefix, refers to radicals of the general formula —O—Ar, wherein —Ar is an aryl.

The term "heteroaryloxy" used alone or as a suffix or prefix, refers to radicals of the general formula —O—Ar', wherein —Ar' is a heteroaryl.

The term "amine" or "amino" used alone or as a suffix or prefix, refers to radicals of the general formula —NRR', wherein R and R' are independently selected from hydrogen or a hydrocarbon radical.

"Acyl" used alone, as a prefix or suffix, means —C(=O)—R, wherein —R is an optionally substituted hydrocarbyl, hydrogen, amino or alkoxy. Acyl groups include, for example, acetyl, propionyl, benzoyl, phenyl acetyl, carboethoxy, and dimethylcarbamoyl.

Halogen includes fluorine, chlorine, bromine and iodine.

"Halogenated," used as a prefix of a group, means one or more hydrogens on the group is replaced with one or more halogens.

"RT" or "rt" means room temperature.

A first ring group being "fused" with a second ring group means the first ring and the second ring share at least two atoms therebetween.

"Link," "linked," or "linking," unless otherwise specified, means covalently linked or bonded.

When a first group, structure, or atom is "directly connected" to a second group, structure or atom, at least one atom of the first group, structure or atom forms a chemical bond with at least one atom of the second group, structure or atom.

"Saturated carbon" means a carbon atom in a structure, molecule or group wherein all the bonds connected to this carbon atom are single bond. In other words, there is no double or triple bonds connected to this carbon atom and this carbon atom generally adopts an sp³ atomic orbital hybridization.

"Unsaturated carbon" means a carbon atom in a structure, molecule or group wherein at least one bond connected to this carbon atom is not a single bond. In other words, there is at least one double or triple bond connected to this carbon atom and this carbon atom generally adopts asp or $sp^2$ atomic orbital hybridization.

In one aspect, an embodiment of the invention provides a compound of Formula I, a pharmaceutically acceptable salt thereof, diastereomers, enantiomers, or mixtures thereof:

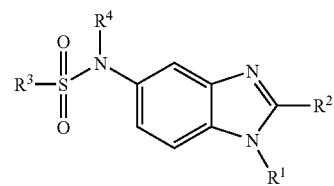

I wherein $R^1$ is selected from $C_{1-10}$alkyl, $C_{2-10}$alkenyl, $C_{2-10}$alkynyl, $R^5R^6N$—$C_{1-6}$alkyl, $R^5O$—$C_{1-6}$alkyl, $R^5C(=O)N(-R^6)$—$C_{1-6}$alkyl, $R^5R^6NS(=O)_2$—$C_{1-6}$alkyl, $R^5CS(=O)_2N(-R^6)$—$C_{1-6}$alkyl, $R^5R^6NC(=O)N(-R^7)$—$C_{1-6}$alkyl, $R^5R^6NS(=O)_2NR^7)$—$C_{1-6}$alkyl, $C_{6-10}$aryl-$C_{1-6}$alkyl, $C_{6-10}$aryl-$C(=O)$-$C_{1-6}$alkyl, $C_{4-8}$cycloalkenyl-$C_{1-6}$alkyl, $C_{3-6}$heterocyclyl-$C_{1-6}$alkyl, $C_{3-6}$heterocyclyl-$C(=O)$—$C_{1-6}$alkyl, $C_{1-10}$hydrocarbylamino, $R^5R^6N$—, $R^{50}$—, $R^5C(=O)N(-R^6)$—, $R^5R^6NS(=O)_2$—, $R^5CS(=O)_2N(-R^6)$—, $R^5R^6NC(=O)N(-R^7)$—, $R^5R^6NS(=O)_2NR^7)$—, $C_{6-10}$aryl, $C_{6-10}$aryl-$C(=O)$—, $C_{3-10}$cycloalkyl, $C_{4-8}$cycloalkenyl, $C_{3-6}$heterocyclyl and $C_{3-6}$heterocyclyl-$C(=O)$—; wherein said $C_{1-10}$alkyl, $C_{2-10}$alkenyl, $C_{2-10}$alkynyl, $C_{6-10}$aryl-$C_{1-6}$alkyl, $C_{6-10}$aryl-$C(=O)$—$C_{1-6}$alkyl, $C_{3-10}$cycloalkyl-$C_{1-6}$alkyl, $C_{4-8}$cycloalkenyl-$C_{1-6}$alkyl, $C_{3-6}$heterocyclyl-$C_{1-6}$alkyl, $C_{3-6}$heterocyclyl-$C(=O)$—$C_{1-6}$alkyl, $C_{1-10}$hydrocarbylamino, $C_{6-10}$aryl, $C_{6-10}$aryl-$C(=O)$—, $C_{3-10}$cycloalkyl, $C_{4-8}$cycloalkenyl, $C_{3-6}$heterocyclyl or $C_{3-6}$heterocyclyl-$C(=O)$— used in defining $R^1$ is optionally substituted by one or more groups selected from halogen, cyano, nitro, methoxy, ethoxy, methyl, ethyl, hydroxy, and —$NR^5R^6$;

$R^2$ is selected from $C_{1-10}$alkyl, $C_{2-10}$alkenyl, $C_{2-10}$alkynyl, $C_{3-10}$cycloalkyl, $C_{3-10}$cycloalkyl-$C_{1-6}$alkyl, $C_{4-8}$cycloalkenyl-$C_{1-6}$alkyl, $C_{3-6}$heterocycloalkyl-$C_{1-6}$alkyl, $C_{4-8}$cycloalkenyl, $R^5R^6N$-, $C_{3-5}$heteroaryl, $C_{6-10}$aryl and $C_{3-6}$heterocycloalkyl, wherein said $C_{1-10}$alkyl, $C_{2-10}$alkenyl, $C_{2-10}$alkynyl, $C_{3-8}$cycloalkyl, $C_{3-8}$cycloalkyl-$C_{1-6}$alkyl, $C_{4-8}$cycloalkenyl-$C_{1-6}$alkyl, $C_{3-6}$heterocycloalkyl-$C_{1-6}$alkyl, $C_{4-8}$cycloalkenyl, $C_{3-5}$heteroaryl, $C_{6-10}$aryl or $C_{3-6}$heterocycloalkyl used in defining $R^2$ is optionally substituted by one or more groups selected from halogen, cyano, nitro, methoxy, ethoxy, methyl, ethyl, hydroxy, and —$NR^5R^6$;

wherein $R^5$, $R^6$ and $R^7$ are independently selected from —H, $C_{1-6}$alkyl, $C_{2-6}$alkenyl, $C_{2-6}$alkynyl, and a divalent $C_{1-6}$group that together with another divalent $R^5$, $R^6$ or $R^7$ forms a portion of a ring;

$R^3$ is selected from —H, $C_{1-10}$alkyl, $C_{2-10}$alkenyl, $C_{2-10}$alkynyl, $C_{3-10}$cycloalkyl, $C_{3-10}$cycloalkyl-$C_{1-6}$alkyl, $C_{4-8}$cycloalkenyl-$C_{1-6}$alkyl, $C_{3-6}$heterocycloalkyl,

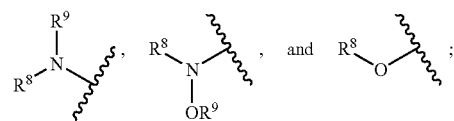

optionally substituted with one or more groups selected from $C_{1-6}$alkyl, halogen, amino and $C_{1-6}$alkoxy;

each of $R^8$ and $R^9$ is independently selected from —H, $C_{2-10}$alkenyl, $C_{2-10}$alkynyl, $C_{3-10}$cycloalkyl, $C_{3-10}$cycloalkyl-$C_{1-6}$alkyl, $C_{3-6}$heterocyclyl, $C_{6-10}$aryl, $C_{3-6}$heterocylcyl-$C_{1-6}$alkyl, $C_{6-10}$aryl-$C_{1-6}$alkyl, and a divalent $C_{1-6}$group that together with another divalent group selected from $R^8$ and $R^9$ forms a portion of a ring, wherein said $C_{1-10}$alkyl, $C_{2-10}$alkenyl, $C_{2-10}$alkynyl, $C_{3-10}$cycloalkyl, $C_{3-10}$cycloalkyl-$C_{1-6}$alkyl, $C_{3-6}$heterocyclyl, $C_{6-10}$aryl, $C_{3-6}$heterocylcyl-$C_{1-6}$alkyl, $C_{6-10}$aryl-$C_{1-6}$alkyl, or divalent $C_{1-6}$group is optionally substituted by one or more groups selected from halogen, cyano, nitro, methoxy, ethoxy, methyl, ethyl, hydroxy, and —NR$^5$R$^6$; and $R^4$ is selected from —H, $C_{1-10}$alkyl, $C_{2-10}$alkenyl, $C_{2-10}$alkynyl, $C_{3-10}$cycloalkyl, $C_{3-10}$cycloalkyl-$C_{1-6}$alkyl, and $C_{4-4}$cycloalkenyl-$C_{1-6}$alkyl.

Another embodiment of the invention provides compounds of Formula I, wherein $R^1$ is selected from $C_{1-4}$alkyl, $C_{2-6}$alkenyl, $C_{2-6}$alkynyl, $C_{3-10}$cycloalkyl-$C_{1-4}$alkyl, $C_{4-6}$cycloalkenyl-$C_{1-4}$alkyl, $C_{3-6}$heterocyclyl-$C_{1-4}$alkyl, $C_{6-10}$aryl, $C_{3-10}$cycloalkyl, $C_{3-6}$heterocyclyl and $C_{4-6}$cycloalkenyl, wherein said $C_{1-6}$alkyl, $C_{2-6}$alkenyl, $C_{2-6}$alkynyl, phenyl-$C_{1-4}$alkyl, $C_{3-10}$cycloalkyl-$C_{1-4}$alkyl, $C_{4-6}$cycloalkenyl-$C_{1-4}$alkyl, $C_{6-10}$aryl, $C_{3-6}$heterocyclyl-$C_{1-4}$alkyl, $C_{3-10}$cycloalkyl, $C_{3-6}$heterocyclyl and $C_{4-6}$cycloalkenyl used in defining $R^1$ is optionally substituted by one or more groups selected from halogen, cyano, nitro, methoxy, ethoxy, methyl, ethyl, hydroxy, and —NR$^5$R$^6$;

$R^2$ is selected from $C_{1-6}$alkyl, $C_{2-6}$alkenyl, $C_{3-6}$cycloalkyl, $C_{3-6}$cycloalkyl-$C_{1-4}$alkyl, $C_{4-6}$cycloalkenyl-$C_{1-4}$alkyl, $C_{3-6}$heterocycloalkyl-$C_{1-4}$alkyl, $C_{4-6}$cycloalkenyl, $C_{3-5}$heteroaryl, R$^5$R$^6$N—, and phenyl, wherein said $C_{1-6}$alkyl, $C_{2-6}$alkenyl, $C_{3-6}$cycloalkyl, $C_{3-6}$cycloalkyl-$C_{1-4}$alkyl, $C_{4-6}$cycloalkenyl-$C_{1-4}$alkyl, $C_{3-6}$heterocycloalkyl-$C_{1-4}$alkyl, $C_{4-6}$cycloalkenyl, $C_{3-5}$heteroaryl, R$^5$R$^6$N—, and phenyl used in defining $R^2$ is optionally substituted by one or more groups selected from halogen, cyano, nitro, methoxy, ethoxy, methyl, ethyl, hydroxy and —NR$^5$R$^6$;

$R^3$ is selected from —H, $C_{2-6}$alkenyl, $C_{3-6}$cycloalkyl, $C_{3-6}$heterocycloalkyl,

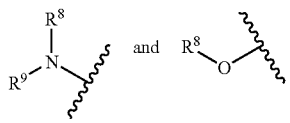

optionally substituted with one or more groups selected from $C_{1-6}$alkyl and halogen;

each of $R^8$ and $R^9$ is independently selected from —H, $C_{1-6}$alkyl, $C_{2-6}$alkenyl, $C_{3-6}$cycloalkyl, $C_{3-6}$cycloalkyl-$C_{1-6}$alkyl, $C_{3-6}$heterocyclyl and $C_{3-6}$heterocylcyl-$C_{1-6}$alkyl, wherein said $C_{1-6}$alkyl, $C_{2-6}$alkenyl, $C_{3-6}$cycloalkyl, $C_{3-6}$cycloalkyl-$C_{1-6}$alkyl, $C_{3-6}$heterocyclyl, $C_{3-6}$heterocylcyl-$C_{1-6}$alkyl, and a divalent $C_{1-6}$group that together with another divalent group selected from $R^8$ and $R^9$ forms a portion of a ring, wherein said $C_{1-6}$alkyl, $C_{2-6}$alkenyl, $C_{3-6}$cycloalkyl, $C_{3-6}$cycloalkyl-$C_{1-6}$alkyl, $C_{3-6}$heterocyclyl and $C_{3-6}$heterocylcyl-$C_{1-6}$alkyl, wherein said $C_{1-6}$alkyl, $C_{2-6}$alkenyl, $C_{3-6}$cycloalkyl, $C_{3-6}$cycloalkyl-$C_{1-6}$alkyl, $C_{3-6}$heterocyclyl, $C_{3-6}$heterocylcyl-$C_{1-6}$alkyl, or divalent $C_{1-6}$group are optionally substituted by one or more groups selected from halogen, cyano, nitro, methoxy, ethoxy, methyl, ethyl, hydroxy and —NR$^5$R$^6$; and $R^4$, $R^5$ and $R^6$ are independently selected from —H and $C_{1-3}$alkyl.

A further embodiment of the invention provides compounds of Formula I, wherein $R^1$ is selected from $C_{1-6}$alkyl, $C_{2-6}$alkenyl, $C_{3-10}$cycloalkyl-$C_{1-4}$alkyl, $C_{4-6}$cycloalkenyl-$C_{1-4}$alkyl, $C_{3-6}$heterocyclcoalkyl-$C_{1-4}$alkyl, $C_{6-10}$aryl, $C_{3-10}$cycloalkcyl, and $C_{4-6}$cycloalkenyl, wherein said $C_{1-6}$alkyl, $C_{2-6}$alkenyl, phenyl-$C_{1-4}$alkyl, $C_{3-10}$cycloalkyl-$C_{1-4}$alkyl, $C_{4-6}$cycloalkenyl-$C_{1-4}$alkyl, $C_{3-6}$heterocylcoalkyl-$C_{1-4}$alkyl, $C_{6-10}$aryl, $C_{3-10}$cycloalkyl, and $C_{4-6}$cycloalkenyl used in defining $R^1$ is optionally substituted by one or more groups selected from halogen, methoxy, ethoxy, methyl, ethyl, hydroxy, and —NR$^5$R$^6$;

$R^2$ is selected from $C_{1-6}$alkyl, $C_{2-6}$alkenyl, $C_{3-6}$cycloalkyl and $C_{3-6}$cycloalkyl-$C_{1-4}$alkyl, wherein said $C_{1-6}$alkyl, $C_{2-6}$alkenyl, $C_{3-6}$cycloalkyl and $C_{3-6}$cycloalkyl-$C_{1-4}$alkyl used in defining $R^2$ is optionally substituted by one or more groups selected from halogen, methoxy, ethoxy, methyl, ethyl, hydroxy and —NR$^5$R$^6$;

$R^3$ is selected from $C_{2-5}$alkyl, $C_{3-6}$heterocycloalkyl,

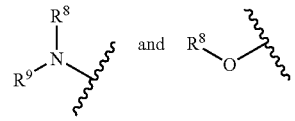

optionally substituted with one or more $C_{1-6}$alkyl;

wherein said $C_{3-6}$heterocycloalkyl contains at least one nitrogen ring atom and the radical of $C_{3-6}$heterocycloalkyl is located on the at least one nitrogen ring atom, and each of $R^8$ and $R^9$ is independently selected from —H, $C_{1-6}$alkyl, morpholinyl-$C_{1-3}$alkyl, pyrrolidinyl-$C_{1-3}$alkyl, and piperidinyl-$C_{1-3}$alkyl, wherein said $C_{1-6}$alkyl, morpholinyl-$C_{1-3}$alkyl, pyrrolidinyl-$C_{1-3}$alkyl, and piperidinyl-$C_{1-3}$alkyl are optionally substituted by one or more groups selected from halogen, methoxy, ethoxy, methyl, ethyl, hydroxy and —NR$^5$R$^6$; and $R^4$, $R^5$ and $R^6$ are independently selected from —H and $C_{1-3}$alkyl.

A further embodiment of the invention provides compounds of Formula I, wherein $R^1$ is selected from cyclohexylmethyl, cyclopentylmethyl, cyclobutylmethyl, cyclopropylmethyl,cyclohexylethyl, cyclopentylethyl, 4,4-difluorocyclohexylmethyl, tetrahydropyranylmethyl, tetrahydropyranylethyl, tetrahydrofuranylmethyl, 1-piperidinylethyl, N-methyl-2-piperidinylmethyl;

$R^2$ is selected from t-butyl, n-butyl, 2-methyl-2-butyl, isopentyl, 2-methoxy-2-propyl, 2-hydroxyl-propyl, trifluoromethyl, 1,1-difluoroethyl, 2,2,2-trifluoroethyl, 1-methyl-propyl, 1,1-dimethyl-propyl, 1,1-dimethyl-3-buten-1-yl, ethyl, and 2-propyl;

$R^3$ is $C_{3-5}$alkyl and

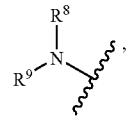

wherein $R^4$, $R^8$ and $R^9$ are selected from —H and $C_{1-3}$alkyl.

It will be understood that when compounds of the present invention contain one or more chiral centers, the compounds of the invention may exist in, and be isolated as, enantiomeric or diastereomeric forms, or as a racemic mixture. The present invention includes any possible enantiomers, diastereomers, racemates or mixtures thereof, of a compound of Formula I. The optically active forms of the compound of the invention may be prepared, for example, by chiral chromatographic-separation of a racemate, by synthesis from optically active starting Materials or by asymmetric synthesis based on the procedures described thereafter.

It will also be appreciated that certain compounds of the present invention may exist as geometrical isomers, for example E and Z isomers of alkenes. The present invention includes any geometrical isomer of a compound of Formula I. It will further be understood that the present invention encompasses tautomers of the compounds of the Formula I.

It will also be understood that certain compounds of the present invention may exist in solvated, for example hydrated, as well as unsolvated forms. It will further be understood that the present invention encompasses all such solvated forms of the compounds of the Formula I.

Within the scope of the invention are also salts of the compounds of the Formula I. Generally, pharmaceutically acceptable salts of compounds of the present invention may be obtained using standard procedures well known in the art, for example by reacting a sufficiently basic compound, for example an alkyl amine with a suitable acid, for example, HCl or acetic acid, to afford a physiologically acceptable anion. It may also be possible to make a corresponding alkali metal (such as sodium, potassium, or lithium) or an alkaline earth metal (such as a calcium) salt by treating a compound of the present invention having a suitably acidic proton, such as a carboxylic acid or a phenol with one equivalent of an alkali metal or alkaline earth metal hydroxide or alkoxide (such as the ethoxide or methoxide), or a suitably basic organic amine (such as choline or meglumine) in an aqueous medium, followed by conventional purification techniques.

In one embodiment, the compound of Formula I above may be converted to a pharmaceutically acceptable salt or solvate thereof, particularly, an acid addition salt such as a hydrochloride, hydrobromide, phosphate, acetate, fumarate, maleate, tartrate, citrate, methanesulphonate orp-toluenesulphonate.

We have now found that the compounds of the invention have activity as pharmaceuticals, in particular as modulators or ligands such as agonists, partial agonists, inverse agonist or antagonists of $CB_1$ receptors. More particularly, the compounds of the invention exhibit activity as agonist of the $CB_1$ receptors and are useful in therapy, especially for relief of various pain conditions such as chronic pain, neuropathic pain, acute pain, cancer pain, pain caused by rheumatoid arthritis, migraine, visceral pain etc. This list should however not be interpreted as exhaustive. Additionally, compounds of the present invention are useful in other disease states in which dysfunction of $CB_1$ receptors is present or implicated. Furthermore, the compounds of the invention may be used to treat cancer, multiple sclerosis, Parkinson's disease, Huntington's chorea, Alzheimer's disease, anxiety disorders, gastrointestinal disorders and cardiovascular disorders.

Compounds of the invention are useful as immunomodulators, especially for autoimmune diseases, such as arthritis, for skin grafts, organ transplants and similar surgical needs, for collagen diseases, various allergies, for use as anti-tumour agents and anti viral agents.

Compounds of the invention are useful in disease states where degeneration or dysfunction of cannabinoid receptors is present or implicated in that paradigm. This may involve the use of isotopically labelled versions of the compounds of the invention in diagnostic techniques and imaging applications such as positron emission tomography (PET).

Compounds of the invention are useful for the treatment of diarrhoea, depression, anxiety and stress-related disorders such as post-traumatic stress disorders, panic disorder, generalized anxiety disorder, social phobia, and obsessive compulsive disorder, urinary incontinence, premature ejaculation, various mental illnesses, cough, lung oedema, various gastro-intestinal disorders, e.g. constipation, functional gastrointestinal disorders such as Irritable Bowel Syndrome and Functional Dyspepsia, Parkinson's disease and other motor disorders, traumatic brain injury, stroke, cardioprotection following miocardial infarction, spinal injury and drug addiction, including the treatment of alcohol, nicotine, opioid and other drug abuse and for disorders of the sympathetic nervous system for example hypertension.

Compounds of the invention are useful as an analgesic agent for use during general anaesthesia and monitored anaesthesia care. Combinations of agents with different properties are often used to achieve a balance of effects needed to maintain the anaesthetic state (e.g. amnesia, analgesia, muscle relaxation and sedation). Included in this combination are inhaled anaesthetics, hypnotics, anxiolytics, neuromuscular blockers and opioids.

Also within the scope of the invention is the use of any of the compounds according to the Formula I above, for the manufacture of a medicament for the treatment of any of the conditions discussed above.

A further aspect of the invention is a method for the treatment of a subject suffering from any of the conditions discussed above, whereby an effective amount of a compound according to the Formula I above, is administered to a patient in need of such treatment.

Thus, the invention provides a compound of Formula I, or pharmaceutically acceptable salt or solvate thereof, as hereinbefore defined for use in therapy.

In a further aspect, the present invention provides the use of a compound of Formula I, or a pharmaceutically acceptable salt or solvate thereof, as hereinbefore defined in the manufacture of a medicament for use in therapy.

In the context of the present specification, the term "therapy" also includes "prophylaxis" unless there are specific indications to the contrary. The term "therapeutic" and "therapeutically" should be contrued accordingly. The term "therapy" within the context of the present invention further encompasses to administer an effective amount of a compound of the present invention, to mitigate either a pre-existing disease state, acute or chronic, or a recurring condition. This definition also encompasses prophylactic therapies for prevention of recurring conditions and continued therapy for chronic disorders.

The compounds of the present invention are useful in therapy, especially for the therapy of various pain conditions including, but not limited to: acute pain, chronic pain, neuropathic pain, back pain, cancer pain, and visceral pain.

In use for therapy in a warm-blooded animal such as a human, the compound of the invention may be administered in the form of a conventional pharmaceutical composition by any route including orally, intramuscularly, subcutaneously, topically, intranasally, intraperitoneally, intrathoracially, intravenously, epidurally, intrathecally, intracerebroventricularly and by injection into the joints.

In one embodiment of the invention, the route of administration may be oral, intravenous or intramuscular.

The dosage will depend on the route of administration, the severity of the disease, age and weight of the patient and other factors normally considered by the attending physician, when determining the individual regimen and dosage level at the most appropriate for a particular patient.

For preparing pharmaceutical compositions from the compounds of this invention, inert, pharmaceutically acceptable carriers can be either solid and liquid. Solid form preparations include powders, tablets, dispersible granules, capsules, cachets, and suppositories.

A solid carrier can be one or more substances, which may also act as diluents, flavoring agents, solubilizers, lubricants, suspending agents, binders, or table disintegrating agents; it can also be an encapsulating material.

In powders, the carrier is a finely divided solid, which is in a mixture with the finely divided compound of the invention, or the active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture in then poured into convenient sized moulds and allowed to cool and solidify.

Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term composition is also intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid form compositions include solutions, suspensions, and emulsions. For example, sterile water or water propylene glycol solutions of the active compounds may be liquid preparations suitable for parenteral administration. Liquid compositions can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

Depending on the mode of administration, the pharmaceutical composition will preferably include from 0.05% to 99% w (percent by weight), more preferably from 0.10 to 50% w, of the compound of the invention, all percentages by weight being based on total composition.

A therapeutically effective amount for the practice of the present invention may be determined, by the use of known criteria including the age, weight and response of the individual patient, and interpreted within the context of the disease which is being treated or which is being prevented, by one of ordinary skills in the art.

Within the scope of the invention is the use of any compound of Formula I as defined above for the manufacture of a medicament.

Also within the scope of the invention is the use of any compound of Formula I for the manufacture of a medicament for the therapy of pain.

Additionally provided is the use of any compound according to Formula I for the manufacture of a medicament for the therapy of various pain conditions including, but not limited to: acute pain, chronic pain, neuropathic pain, back pain, cancer pain, and visceral pain.

A further aspect of the invention is a method for therapy of a subject suffering from any of the conditions discussed above, whereby an effective amount of a compound according to the Formula I above, is administered to a patient in need of such therapy.

Additionally, there is provided a pharmaceutical composition comprising a compound of Formula I, or a pharmaceutically acceptable salt thereof, in association with a pharmaceutically acceptable carrier.

Particularly, there is provided a pharmaceutical composition comprising a compound of Formula I, or a pharmaceutically acceptable salt thereof, in association with a pharmaceutically acceptable carrier for therapy, more particularly for therapy of pain.

Further, there is provided a pharmaceutical composition comprising a compound of Formula I, or a pharmaceutically acceptable salt thereof, in association with a pharmaceutically acceptable carrier use in any of the conditions discussed above.

Another aspect of the invention is a method of preparing the compounds of the present invention.

In one embodiment, the method of the invention is a method for preparing a compound of Formula I,

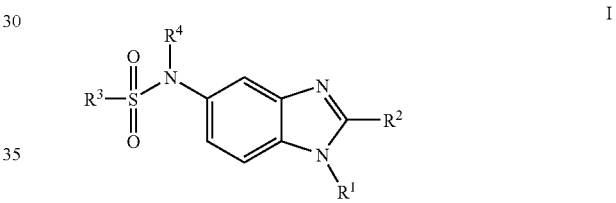

comprising the step of reacting a compound of Formula II,

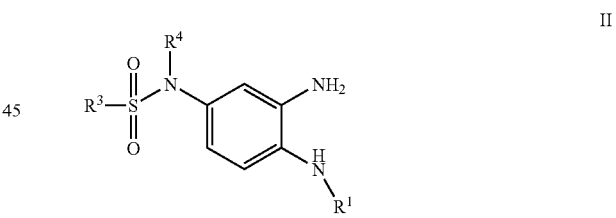

with a compound of $R^2COX$, in the presence of a base, such as an alkylamine, and optionally a coupling reagent, such as HATU, EDC, followed by treatment with an acid such as AcOH,
wherein
X is selected from Cl, Br, F and OH;
$R^1$ is selected from $C_{1-10}$alkyl, $C_{2-10}$alkenyl, $C_{2-10}$alkynyl, $R^5R^6N$—$C_{1-6}$alkyl, $R^5O$—$C_{1-6}$ alkyl, $R^5C(=O)N(-R^6)$—$C_{1-6}$alkyl, $R^5R^6NS(=O)_2$—$C_{1-6}$alkyl, $R^5CS(=O)_2N(-R^6)$—$C_{1-6}$alkyl, $R^5R^6NC(=O)N(-R^7)$—$C_{1-6}$alkyl, $R^5R^6NS(=O)_2N(R^7)$—$C_{1-6}$alkyl, $C_{6-10}$aryl-$C_{1-6}$alkyl, $C_{6-10}$aryl-$C(=O)$—$C_{1-6}$alkyl, $C_{4-8}$cycloalkenyl-$C_{1-6}$alkyl, $C_{3-6}$heterocyclyl-$C_{1-6}$alkyl, $C_{3-6}$heterocyclyl-$C(=O)$—$C_{1-6}$alkyl, $C_{1-10}$hydrocarbylamino, $R^5R^6N$—, $R^5O$—, $R^5C(=O)N(-R^6)$—, $R^5R^6NS(=O)_2$—, $R^5CS(=O)_2N(-R^6)$—, $R^5R^6NC(=O)N(-R^7)$—, $R^5R^6NS(=O)_2N(R^7)$—, $C_{6-10}$aryl, $C_{6-10}$aryl-$C(=O)$—, $C_{3-10}$cycloalkyl, $C_{4-8}$cycloalkenyl, $C_{3-6}$heterocyclyl and $C_{3-6}$heterocyclyl-C(=O)—; wherein said $C_{1-10}$alkyl, $C_{2-10}$alkenyl, $C_{6-10}$aryl-$C_{1-6}$alkyl, $C_{6-10}$aryl-C(=O)—$C_{1-6}$alkyl, $C_{3-10}$cycloalkyl-$C_{1-6}$alkyl, $C_{4-8}$cycloalkenyl-$C_{1-6}$alkyl, $C_{3-6}$heterocyclyl-$C_{1-6}$alkyl, $C_{3-6}$heterocyclyl-C(=O)—$C_{1-6}$alkyl, $C_{1-10}$hydrocarbylamino, $C_{6-10}$aryl, $C_{6-10}$aryl-C(=O)—, $C_{4-8}$cycloalkenyl, $C_{3-6}$heterocyclyl or $C_{3-6}$heterocyclyl-C(=O)— used in defining $R^1$ is optionally substituted by one or more groups selected from halogen, cyano, nitro, methoxy, ethoxy, methyl, ethyl, hydroxy, and —$NR^5R^6$;

$R^2$ is selected from $C_{1-10}$alkyl, $C_{2-10}$alkenyl, $C_{2-10}$alkynyl, $C_{3-10}$cycloalkyl, $C_{3-10}$cycloalkyl-$C_{1-6}$alkyl, $C_{4-8}$cycloalkenyl-$C_{1-6}$alkyl, $C_{3-6}$heterocycloalkyl-$C_{1-6}$alkyl, $C_{4-8}$cycloalkenyl, $R^5R^6N$—, $C_{3-5}$heteroaryl, $C_{6-10}$aryl and $C_{3-6}$heterocycloalkyl, wherein said $C_{1-10}$alkyl, $C_{2-10}$alkenyl, $C_{2-10}$alkynyl, $C_{3-8}$cycloalkyl, $C_{3-8}$cycloalkyl-$C_{1-6}$alkyl, $C_{4-8}$cycloalkenyl-$C_{1-6}$alkyl, $C_{3-6}$heterocycloalkyl-$C_{1-6}$alkyl, $C_{4-8}$cycloalkenyl, $C_{3-5}$heteroaryl, $C_{6-10}$aryl or $C_{3-6}$heterocycloalkyl used in defining $R^2$ is optionally substituted by one or more groups selected from halogen, cyano, nitro, methoxy, ethoxy, methyl, ethyl, hydroxy, and —$NR^5R^6$;

wherein $R^5$, $R^6$ and $R^7$ are independently selected from —H, $C_{1-6}$alkyl, $C_{2-6}$alkenyl, $C_{2-6}$alkynyl, and a divalent $C_{1-6}$group that together with another divalent $R^5$, $R^6$ or $R^7$ forms a portion of a ring;

$R^3$ is selected from —H, $C_{1-10}$alkyl, $C_{2-10}$alkenyl, $C_{2-10}$alkynyl, $C_{3-10}$cycloalkyl, $C_{3-10}$cycloalkyl-$C_{1-6}$alkyl, $C_{4-8}$cycloalkenyl-$C_{1-6}$alkyl, $C_{3-6}$heterocycloalkyl,

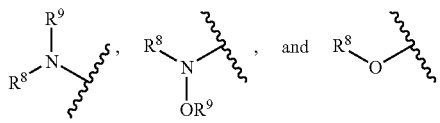

optionally substituted with one or more groups selected from $C_{1-6}$alkyl, halogen, amino and $C_{1-6}$alkoxyl;

each of $R^8$ and $R^9$ is independently selected from —H, $C_{1-10}$alkyl, $C_{2-10}$alkenyl, $C_{2-10}$alkynyl, $C_{3-10}$cycloalkyl, $C_{3-10}$cycloalkyl-$C_{1-6}$alkyl, $C_{3-6}$heterocyclyl, $C_{6-10}$aryl, $C_{3-6}$heterocyclyl-$C_{1-6}$alkyl, $C_{6-10}$aryl-$C_{1-6}$alkyl, and a divalent $C_{1-6}$group that together with another divalent group selected from $R^8$ and $R^9$ forms a portion of a ring, wherein said $C_{1-10}$alkyl, $C_{2-10}$alkenyl, $C_{2-10}$alkynyl, $C_{3-10}$cycloalkyl, $C_{3-10}$cycloalkyl-$C_{1-6}$alkyl, $C_{3-6}$heterocyclyl, $C_{6-10}$aryl, $C_{3-6}$heterocyclyl-$C_{1-6}$alkyl, $C_{6-10}$aryl-$C_{1-6}$alkyl, or divalent $C_{1-6}$group is optionally substituted by one or more groups selected from halogen, cyano, nitro, methoxy, ethoxy, methyl, ethyl, hydroxy, and —$NR^5R^6$; and $R^4$ is selected from —H, $C_{1-10}$alkyl, $C_{2-10}$alkenyl, $C_{2-10}$alkynyl, $C_{3-10}$cycloalkyl, $C_{3-10}$cycloalkyl-$C_{1-6}$alkyl, and $C_{4-8}$cycloalkenyl-$C_{1-4}$alkyl.

Particularly, the method of the invention is a method of preparing a compound of Formula I, wherein X is selected from Cl, Br, F and OH;

$R^1$ is selected from $C_{1-6}$alkyl, $C_{2-6}$alkenyl, phenyl-$C_{1-4}$alkyl, $C_{3-10}$cycloalkyl-$C_{1-4}$alkyl, $C_{4-6}$cycloalkenyl-$C_{1-4}$alkyl, $C_{6-10}$aryl, $C_{3-6}$heterocyclyl-$C_{1-4}$alkyl, $C_{3-10}$cycloalkyl, and $C_{4-6}$cycloalkenyl, wherein said $C_{1-6}$alkyl, $C_{2-6}$alkenyl, phenyl-$C_{1-4}$alkyl, $C_{3-10}$cycloalkyl-$C_{1-4}$alkyl, $C_{4-6}$cycloalkenyl-$C_{1-4}$alkyl, $C_{6-10}$aryl, $C_{3-6}$heterocyclyl-$C_{1-4}$ alkyl, $C_{3-10}$cycloallyl, and $C_{4-6}$cycloalkenyl used in defining $R^1$ is optionally substituted by one or more groups selected from halogen, methoxy, ethoxy, methyl, ethyl, hydroxy, and —$NR^5R^6$;

$R^2$ is selected from $C_{1-6}$alkyl, $C_{2-6}$alkenyl, $C_{3-6}$cycloalkyl and $C_{3-6}$cycloalkyl-$C_{1-4}$alkyl, wherein said $C_{1-6}$alkyl, $C_{2-6}$alkenyl, $C_{3-6}$cycloalkyl and $C_{3-6}$cycloalkyl-$C_{1-4}$alkyl used in defining $R^2$ is optionally substituted by one or more groups selected from halogen, methoxy, ethoxy, methyl, ethyl, hydroxy and —$NR^5R^6$;

$R^3$ is selected from —H, $C_{2-5}$alkyl, $C_{3-6}$heterocycloalkyl,

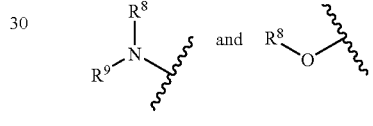

optionally subsitituted with one or more $C_{1-6}$alkyl;

wherein said $C_{3-6}$heterocycloalkyl contains at least one nitrogen ring atom and the radical of $C_{3-6}$heterocycloalkyl is located on the at least one nitrogen ring atom, and each of $R^8$ and $R^9$ is independently selected from —H, $C_{1-6}$alkyl, morpholinyl-$C_{1-3}$alkyl, pyrrolidinyl-$C_{1-3}$alkyl, and piperidinyl-$C_{1-3}$alkyl, wherein said $C_{1-6}$alkyl, morpholinyl-$C_{1-3}$alkyl, pyrrolidinyl-$C_{1-3}$alkyl, and piperidinyl-$C_{1-3}$alkyl are optionally substituted by one or more groups selected from halogen, methoxy, ethoxy, methyl, ethyl, hydroxy and —$NR^5R^6$; and $R^4$, $R^5$ and $R^6$ are independently selected from —H and $C_{1-3}$alkyl.

Compounds of the present invention may also be prepared according to the synthetic routes as depicted in Scheme 1.

Scheme 1.

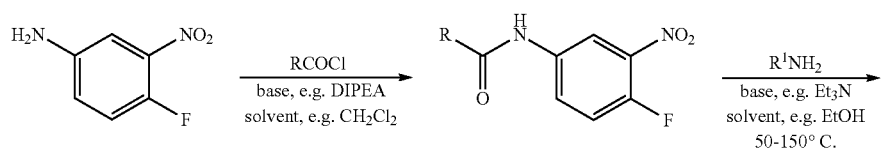

-continued

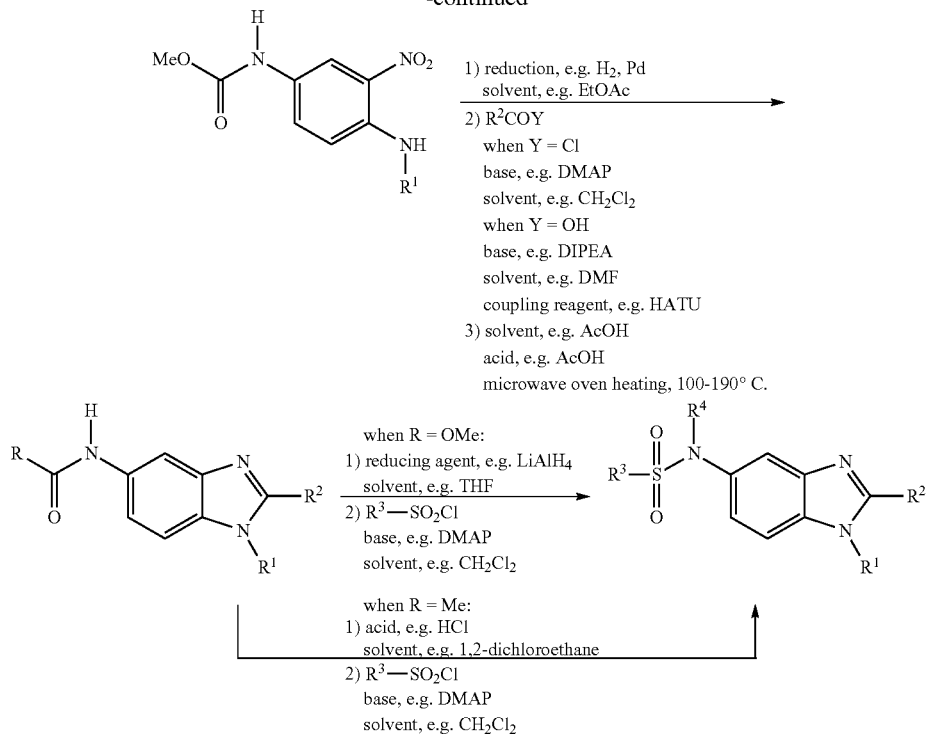

R$^1$, R$^2$, R$^3$ and R$^4$ are as defined in the specifications.

Biological Evaluation hCB$_1$ and hCB$_2$ Receptor Binding

Human CB$_1$ receptor from Receptor Biology (hCB$_1$) or human CB$_2$ receptor from BioSignal (hCB2) membranes are thawed at 37° C., passed 3 times through a 25-gauge blunt-end needle, diluted in the cannabinoid binding buffer (50 mM Tris, 2.5 mM EDTA, 5 mM MgCl$_2$, and 0.5 mg/mL BSA fatty acid free, pH 7.4) and aliquots containing the appropriate amount of protein are distributed in 96-well plates. The IC$_{50}$ of the compounds of the invention at hCB$_1$ and hCB$_2$ are evaluated from 10-point dose-response curves done with $^3$H-CP55,940 at 20000 to 25000 dpm per well (0.17-0.21 nM) in a final volume of 300 µl. The total and non-specific binding are determined in the absence and presence of 0.2 µM of HU210 respectively. The plates are vortexed and incubated for 60 minutes at room temperature, filtered through Unifilters GF/B (presoaked in 0.1% polyethyleneimine) with the Tomtec or Packard harvester using 3 mL of wash buffer (50 mM Tris, 5 mM MgCl$_2$, 0.5 mg BSA pH 7.0). The filters are dried for 1 hour at 55° C. The radioactivity (cpm) is counted in a TopCount (Packard) after adding 65 µl/well of MS-20 scintillation liquid.

hCB$_1$ and hCB$_2$ GTPγS Binding

Human CB$_1$ receptor from Receptor Biology (hCB$_1$) or human CB$_2$ receptor membranes (BioSignal) are thawed at 37° C., passed 3 times through a 25-gauge blunt-end needle and diluted in the GTPγS binding buffer (50 mM Hepes, 20 mM NaOH, 100 mM NaCl, 1 mM EDTA, 5 mM MgCl$_2$, pH 7.4, 0.1% BSA). The EC$_{50}$ and E$_{max}$ of the compounds of the invention are evaluated from 10-point dose-response curves done in 300 µl with the appropriate amount of membrane protein and 100000-130000 dpm of GTPg$^{35}$S per well (0.11-0.14 nM). The basal and maximal stimulated binding is determined in absence and presence of 1 µM (hCB$_2$) or 10 µM (hCB$_1$) Win 55, 212-2 respectively. The membranes are pre-incubated for 5 minutes with 56.25 µM (hCB2) or 112.5 µM (hCB$_1$) GDP prior to distribution in plates (15 M (hCB$_2$) or 30 µM (hCB$_1$) GDP final). The plates are vortexed and incubated for 60 minutes at room temperature, filtered on Unifilters GF/B (presoaked in water) with the Tomtec or Packard harvester using 3 ml of wash buffer (50 mM Tris, 5 mM MgCl$_2$, 50 mM NaCl, pH 7.0). The filters are dried for 1 hour at 55° C. The radioactivity (cpm) is counted in a TopCount (Packard) after adding 65 µl/well of MS-20 scintillation liquid. Antagonist reversal studies are done in the same way except that (a) an agonist dose-response curve is done in the presence of a constant concentration of antagonist, or (b) an antagonist dose-response curve is done in the presence of a constant concentration of agonist.

Based on the above assays, the dissociation constant (Ki) for a particular compound of the invention towards a particular receptor is determined using the following equation:

$$Ki=IC_{50}/(1+[rad]/Kd),$$

Wherein IC$_{50}$ is the concentration of the compound of the invention at which 50% displacement has been observed;

[rad] is a standard or reference radioactive ligand concentration at that moment; and Kd is the dissociation constant of the radioactive ligand towards the particular receptor.

Using the above-mentioned assays, the Ki towards human CB$_1$ receptors for most compounds of the invention is measured to be in the range of 5-25 nM. The Ki towards human CB$_2$ receptors for most compounds of the invention is measured to be in the range of about 0.7-3.5 nM. The EC$_{50}$ towards human CB$_1$ receptors for most compounds of the invention is measured to be in the range of about 24-84 nM.

The $E_{max}$ towards human $CB_1$ receptors for most compounds of the invention is measured to be in the range of about 105-116%.

EXAMPLES

The invention will further be described in more detail by the following Examples which describe methods whereby compounds of the present invention may be prepared, purified, analyzed and biologically tested, and which are not to be construed as limiting the invention.

Example 1

N-[2-tert-Butyl-1-(cyclohexylmethyl)-1H-benzimidazol-5-yl]-N,N',N'-trimethylsulfamide

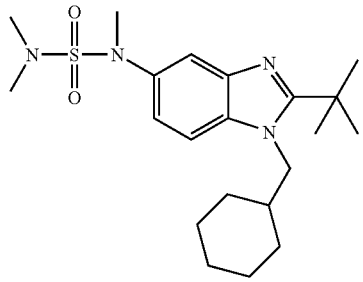 [SMILES: CN(C)S(=O)(=O)N(C)c1ccc2c(c1)nc(C(C)(C)C)n2CC1CCCCC1]

Step A. N-[2-tert-Butyl-1-(cyclohexylmethyl)-1H-benzimidazol-5-yl]-N,N',N'-trimethylsulfamide

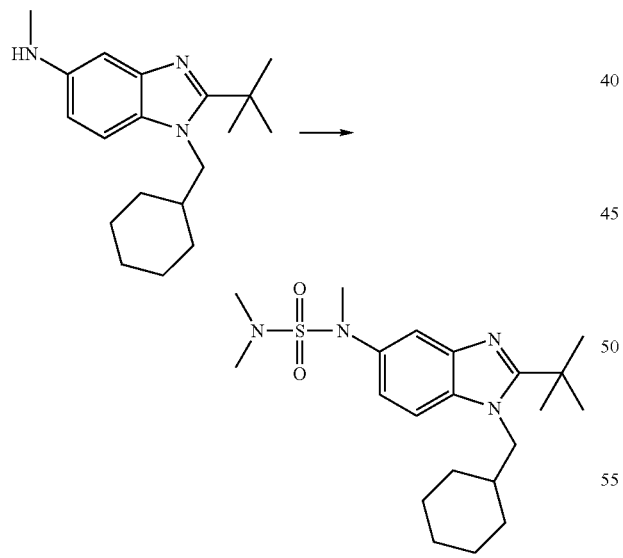

2-tert-Butyl-1-(cyclohexylmethyl)-N-methyl-1H-benzimidazol-5-amine (40 mg, 0.133 mmol) (for preparation, see the following steps B, C, D, E and F) and dimethylsulfamoyl chloride (0.020 mL, 0.173 mmol) were stirred in 3 mL of dichloromethane containing a catalytic amount of DMAP overnight at rt. The solvent was evaporated. The product was purified by reversed-phase HPLC using 20-80% $CH_3CN/H_2O$ and then lyophilized affording the title compound as the corresponding TFA salt. Yield: 36 mg (52%); $^1H$ NMR (400 MHz, METHANOL-$D_4$) δ 1.22 (m, 5H), 1.62 (m, 2H), 1.65 (s, 9H), 1.67 (m, 1H), 1.75 (m, 2H), 2.10 (m, 1H), 2.81 (s, 6H), 3.29 (s, 3H), 4.44 (d, J=7.62 Hz, 2H), 7.64 (dd, J=9.08, 2.05 Hz, 1H), 7.78 (d, J=1.95 Hz, 1H), 7.90 (d, J=8.98 Hz, 1H); MS (ESI) $(M+H)^+$ 407.3; Anal. Calcd for $C_{21}H_{34}N_4O_2S$+1.3 TFA+0.3 $H_2O$: C, 50.60; H, 6.46; N, 10.00. Found: C, 50.64; H, 6.47; N, 10.15.

Step B. Methyl (4-fluoro-3-nitrophenyl)carbamate

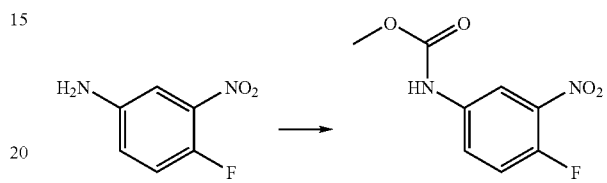

Methyl chloroformate (13.2 mL, 170.2 mmol) was added dropwise to a cold (0° C.) dichloromethane (200 mL) solution of 4-fluoro-3-nitro aniline (24.15 g, 154.7 mmol) and DIPEA (35 mL, 201 mmol). The reaction mixture was stirred at rt overnight. The solution was then diluted with 200 mL of dichloromethane and washed with 2M HCl, brine and dried over anhydrous $MgSO_4$. The solvent was concentrated and the product was directly used for next step without further purification. Yield: 35.5 g (99%); $^1H$ NMR (400 MHz, CHLOROFORM-D) δ 3.81 (s, 3H), 7.02 (s, 1H), 7.23 (m, 1H), 7.72 (d, J=8.59 Hz, 1H), 8.17 (dd, J=6.35, 2.64 Hz, 1H).

Step C. Methyl {4-[(cyclohexylmethyl)amino]-3-nitrophenyl}carbamate

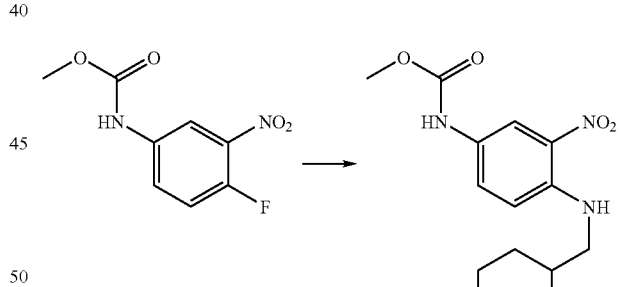

Methyl (4-fluoro-3-nitrophenyl)carbamate (1.00 g, 4.67 mmol) and cyclohexylmethyl amine (0.730 mL, 5.60 mmol) were stirred in EtOH (20 mL) containing TEA (1.0 mL, 7.00 mmol) at 75° C. for 24 h. The solvent was concentrated. The residue was dissolved in EtOAc and washed with 5% $KHSO_4$ solution, saturated $NaHCO_3$ solution, brine and dried over anhydrous $MgSO_4$. The crude product was purified by flash chromatography using 4:1/hex:EtOAc on silica gel. Yield: 1.05 g (73%); $^1H$ NMR (400 MHz, CHLOROFORM-D) δ 1.04 (ddd, J=24.02, 12.11, 2.93 Hz, 2H), 1.25 (m, 3H), 1.69 (m, 2H), 1.76 (m, 1H), 1.79 (m, 1H), 1.83 (m, 1H), 1.86 (m, 1H), 3.14 (dd, J=6.44, 5.66 Hz, 2H), 3.78 (s, 3H), 6.46 (m, 1H), 6.84 (d, J=9.37 Hz, 1H), 7.63 (m, 1H), 8.05 (d, J=2.54 Hz, 1H), 8.09 (m, 1H).

Step D. Methyl {3-amino-4-[(cyclohexylmethyl)amino]phenyl}carbamate

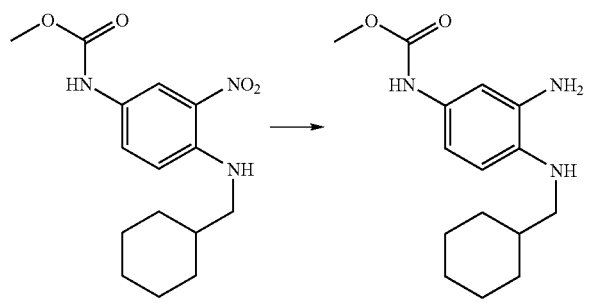 [SMILES: COC(=O)Nc1ccc(NCC2CCCCC2)c([N+](=O)[O-])c1 ; COC(=O)Nc1ccc(NCC2CCCCC2)c(N)c1]

Methyl {4-[(cyclohexylmethyl)amino]-3-nitrophenyl}carbamate (1.05 g, 3.42 mmol) was dissolved in 30 mL of EtOAc containing a catalytic amount of 10% Pd/C. The solution was shaken in a Parr hydrogenation apparatus under $H_2$ atmosphere (40 psi) at rt overnight. The solution was filtered through Celite and the solvent evaporated. The product was directly used for the next step without further purification. Yield: 950 mg (99%). MS (ESI) (M−1−H)$^+$ 277.9.

Step E. Methyl [2-tert-butyl-1-(cyclohexylmethyl)-1H-benzimidazol-5-yl]carbamate

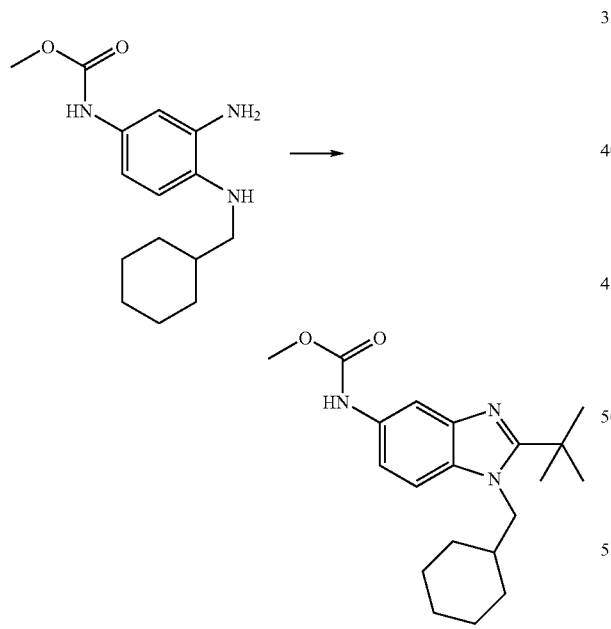

Methyl {3-amino-4-[(cyclohexylmethyl)amino]phenyl}carbamate (950 mg, 3.43 mmol) and DMAP (100 mg, 0.858 mmol) were dissolved in 25 mL of dichloromethane. Trimethylacetyl chloride (0.460 mL, 3.77 mmol) was added in dropwise and the solution was stirred at rt for 1 h. The solvent was concentrated. The residue was divided in two portions and each of them was dissolved in 3 mL of glacial AcOH in a sealed tube. The solutions were heated at 150° C. using a Personal Chemistry Smith Synthesizer microwave instrument for three intervals of 30 min (3×30 min). The contents of the two tubes were combined and the solvent was evaporated. The residue was dissolved in EtOAc and washed with saturated $NaHCO_3$ solution, brine and dried over anhydrous $MgSO_4$. The crude product was purified by flash chromatography using 3:1/dichloromethane:diethyl ether. Yield: 656 mg (56%); $^1$H NMR (400 MHz, CHLOROFORM-D) δ 1.08 (m, 2H), 1.18 (m, 3H), 1.54 (s, 9H), 1.65 (m, 1H), 1.69 (m, 2H), 1.73 (dd, J=5.96, 3.22 Hz, 2H), 2.02 (m, 1H), 3.78 (s, 3H), 4.10 (d, J=7.42 Hz, 2H), 6.64 (m, 1H), 7.25 (d, J=8.79 Hz, 1H), 7.39 (m, 1H), 7.59 (d, J=1.76 Hz, 1H).

Step F. 2-tert-Butyl-1-(cyclohexylmethyl)-N-methyl-1H-benzimidazol-5-amine

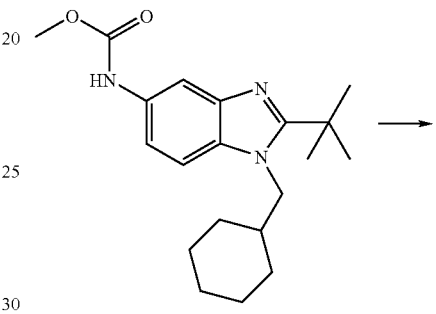

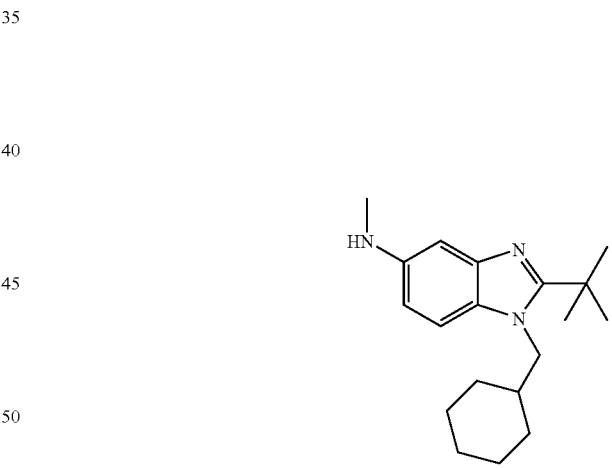

Methyl [2-tert-butyl-1-(cyclohexylmethyl)-1H-benzimidazol-5-yl]carbamate (650 mg, 1.89 mmol) was dissolved in 20 mL of THF at 0° C. under nitrogen. 1M HCl/ether (2.65 mL, 2.65 mmol) was added dropwise and the solution was stirred at 0° C. for 15 min. LiAlH$_4$ (360 mg, 9.45 mmol) was then slowly added and the solution was stirred at rt overnight. The reaction mixture was quenched at 0° C. by addition of MeOH (5 mL) followed by water (10 mL). The solution was diluted with EtOAc and washed with saturated NaHCO$_3$ solution, brine and dried over anhydrous MgSO$_4$. The solvent was evaporated and the product was used directly for Step A without further purification. Yield: 544 mg (96%). $^1$H NMR (400 MHz, CHLOROFORM-D) δ 1.08 (s, 2H), 1.17 (m, 3H), 1.54 (s, 9H), 1.64 (m, 2H), 1.67 (m, 2H), 1.72 (m, 2H), 2.02

(m, 1H), 2.87 (s, 3H), 4.06 (d, J=7.62 Hz, 2H), 6.60 (dd, J=8.69, 2.25 Hz, 1H), 7.00 (d, J=1.76 Hz, 1H), 7.12 (d, J=8.59 Hz, 1H).

Example 2

N-[2-tert-Butyl-1-(cyclohexylmethyl)-1H-benzimidazol-5-yl]-N',N'-diethyl-N-methylsulfamide

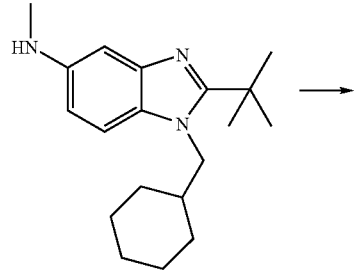

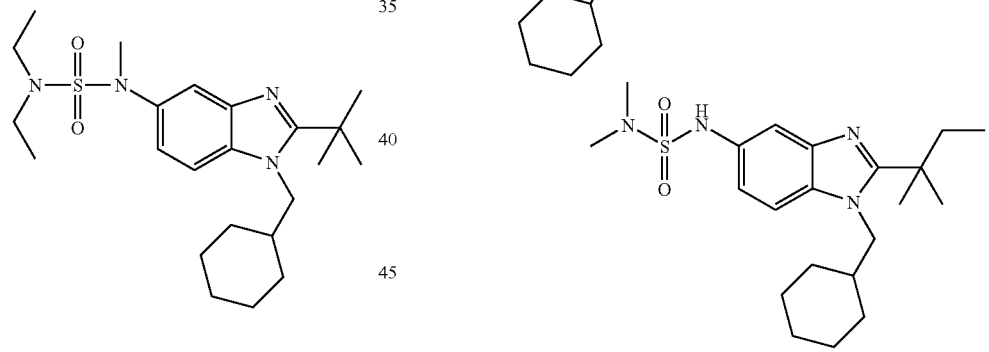

A solution of diethylamine (0.103 mL, 1.00 mmol) in 1 mL dichloromethane and TEA (0.140 mL, 1.00 mmol) were added sequentially to a cold (0° C.) solution of SO$_2$Cl$_2$ (0.160 mL, 2.00 mmol) in dichloromethane (1 mL) under a nitrogen atmosphere. The solution was then stirred at rt for 3 h. The solution was washed with 5% KHSO$_4$ solution, brine and dried over anhydrous MgSO$_4$. The solvent was concentrated. The residue was then dissolved in 1 mL of dichloromethane, to which a solution of 2-tert-butyl-1-(cyclohexylmethyl)-N-methyl-1H-benzimidazol-5-amine (25 mg, 0.0835 mmol) and DMAP (catalytic) in 1 mL of dichloromethane was added dropwise. The solution was stirred at rt for 24 h. The product was purified by reversed-phase HPLC using 30-80% CH$_3$CN/H$_2$O and lyophilized affording the title compound as the corresponding TFA salt. Yield: 15 mg (33%); $^1$H NMR (400 MHz, METHANOL-D$_4$) δ 1.13 (t, J=7.13 Hz, 6H), 1.24 (m, 5H), 1.63 (m, 2H), 1.67 (s, 9H), 1.70 (m, 1H), 1.77 (m, 2H), 2.12 (m, 1H), 3.26 (s, 3H), 3.30 (m, 4H), 4.46 (d, J=7.62 Hz, 2H), 7.61 (dd, J=8.98, 2.15 Hz, 1H), 7.78 (d, J=1.95 Hz, 1H), 7.89 (d, J=8.98 Hz, 1H); MS (ESI) (M+H)$^+$ 435.2; Anal. Calcd for C$_{23}$H$_{38}$N$_4$O$_2$S+1.2 TFA+0.8 H$_2$O: C, 52.07; H, 7.02; N, 9.56. Found: C, 52.00; H, 7.01; N, 9.55.

Example 3

N'-[1-(cyclohexylmethyl)-2-(1,1-dimethylpropyl)-1H-benzimidazol-5-yl]-N,N-dimethyl-sulfamide

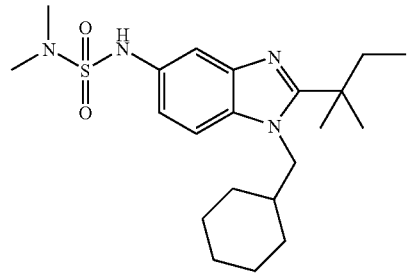 [SMILES: CCC(C)(C)c1nc2cc(NS(=O)(=O)N(C)C)ccc2n1CC1CCCCC1]

Step A. N'-[1-(cyclohexylmethyl)-2-(1,1-dimethylpropyl)-1H-benzimidazol-5-yl]-N,N-dimethyl-sulfamide DMAP (80.1 mg, 0.65 mmol) was added to a solution of 1-(cyclohexylmethyl)-2-(1,1-dimethylpropyl)-1H-benzimidazol-5-amine (69.5 mg, 0.18 mmol) (for preparation, see the following steps B, C, D, E and F) in acetonitrile (10 mL) at 0° C., followed by addition of dimethylsulfamoyl chloride (22 uL, 28.7 mg, 0.20 mmol). The resulting mixture was heated at reflux for 20 h and then quenched with MeOH (2 mL). After evaporation of the solvent, the residue was dissolved in EtOAc (100 mL) and washed with NaCl aqueous solution (10 mL) and dried over Na$_2$SO$_4$. After filtration and evaporation, the residue was purified by MPLC (hexanes/EtOAc 1:1 as eluent on silica gel) to give the title compound as a white solid (56.2 mg, 76%), which was converted to a white solid as a TFA salt. $^1$H NMR (400 MHz, CD$_3$OD): δ 0.84 (t, J=7.52 Hz, 3H), 1.24 (m, 5H), 1.64 (m, 2H), 1.66 (s, 6 μl), 1.71 (m, 1H), 1.78 (m, 2H), 2.01 (q, J=7.55 Hz, 2H), 2.11 (m, 1H), 2.82 (s, 6H), 4.44 (d, J=7.81 Hz, 2H), 7.37 (dd, J=8.98, 2.15 Hz, 1H), 7.69 (d, J=2.15 Hz, 1H), 7.84 (d, J=8.98 Hz, 1H); MS (ESI)

(M+H)⁺: 407.3; Anal. Calcd for $C_{21}H_{34}N_4O_2S+1.0\,TFA+0.2\,H_2O$: C, 52.70; H, 6.81; N, 10.69. Found: C, 52.70; H, 6.66; N, 10.45.

Step B. N-(4-fluoro-3-nitrophenyl)acetamide

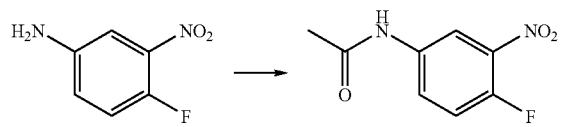

4-Fluoro-3-nitro-aniline (45.0 g, 288.2 mmol) was added portionwise to acetic anhydride (150 mL) at room temperature. The reaction mixture was stirred at room temperature for 2 h. The white solid was collected and dried in vacuo to give the title compound (42.0 g, 70%). ¹H NMR (400 MHz, CDCl₃): δ 2.23 (s, 3H), 7.26 (m, 1 H), 7.50 (s broad, 1H), 7.87 (m, 1H), 8.23 (dd, J=6.44, 2.73 Hz, 1H).

Step C. N-{4-[(cyclohexylmethyl)amino]-3-nitrophenyl}acetamide

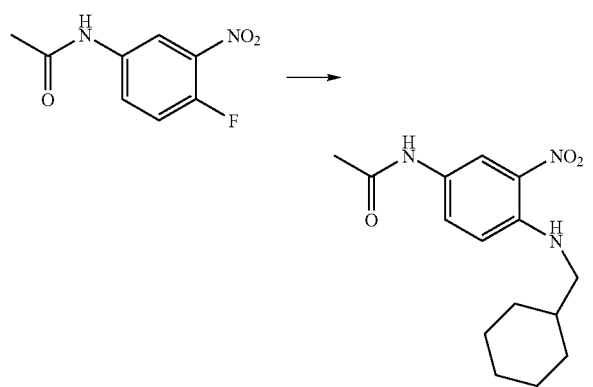

Cyclohexylmethylamine (2.86 mL, 2.49 g, 22.0 mmol) was added to a mixture of N-(4-fluoro-3-nitrophenyl)acetamide (3.96 g, 20.0 mmol) and sodium carbonate (4.66 g, 44 mmol) in EtOH (50 mL) at room temperature. The reaction mixture was heated for 48 h at 60° C., and diluted with H₂O (800 mL). The orange solid was precipitated out and collected to give the desired product (6.60 g, 100%). MS (ESI) (M+H)⁺: 292.32.

Step D. N-{3-amino-4-[(cyclohexylmethyl)amino] phenyl}acetamide

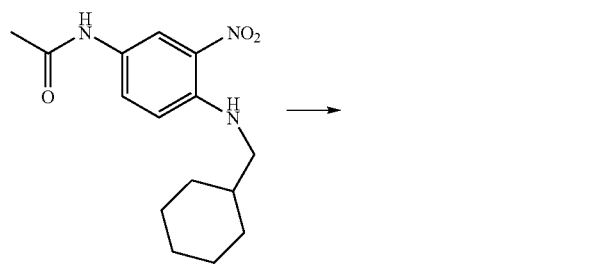

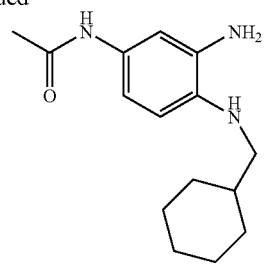

The above crude product N-{4-[(cyclohexylmethyl)amino]-3-nitrophenyl}acetamide (6.60 g) was hydrogenated in ethyl acetate (300 mL) catalyzed by 10% Pd/C (0.5 g) at 20-30 psi H₂ in Parr shaker for 4.5 h at room temperature. After filtration through celite and concentration, 5.08 g (97%) of a purple solid was obtained. which was used in the next step without further purification. ¹H NMR (400 MHz, CDCl₃): δ 1.00 (m, 2H), 1.24 (m, 3H), 1.59 (m, 2H), 1.72 (m, 2H), 1.84 (m, 2H), 2.13 (s, 3H), 2.91 (d, J=6.64 Hz, 2H), 3.37 (s broad, 3H), 6.56 (d, J=8.40 Hz, 1H), 6.69 (dd, J=8.30, 2.25 Hz, 1H), 6.98 (s, 1H), 7.12 (d, J=2.34 Hz, 1H). MS (ESI) (M+H)⁺: 262.31.

Step E. N-[1-(cyclohexylmethyl)-2-(1,1-dimethyl-propyl)-1H-benzimidazol-5-yl]acetamide DMAP (0.65 g, 5.3 mmol) was added to a suspension of N-{3-amino-4-[(cyclohexylmethyl)amino]

phenyl}acetamide (2.09 g, 8.0 mmol) in dichloromethane (40 mL) at −10° C., followed by addition of 2,2-dimethylbutyryl chloride (1.51 g, 11.2 mmol). The resulting mixture was stirred overnight at room temperature. After evaporation of the solvent, 4.14 g of a brown solid was obtained, which was consistent with the desired coupling product A. MS (ESI) (M+H)⁺=360.07. 308.1 mg of the above crude product A was dissolved in 1,2-dichloroethane (5 mL) in a Teflon-capped test tube. The vessel was irradiated by microwave for 3 h at 170° C. Upon evaporation of the solvent, the residue was dissolved in EtOAc (100 mL), washed with 2N NaOH aqueous solution (10 mL), saturated NaCl aqueous solution (10 mL) and dried over $Na_2SO_4$. After filtration and evaporation, the residue was purified by MPLC (hexanes/EtOAc 1:1 as eluent on silica gel) to give the title compound as a light yellow solid (111.0 mg, 55%), which was converted to a white solid as a TFA salt. ¹H NMR (400 MHz, $CD_3OD$): δ 0.84 (t, J=7.52 Hz, 3H), 1.25 (m, 5H), 1.63 (m, 2H), 1.66 (s, 6H), 1.70 (m, 1H), 1.77 (m, 2H), 2.01 (q, J=7.42 Hz, 2H), 2.10 (m, 1H), 2.18 (s, 3H), 4.44 (d, J=7.81 Hz, 2H), 7.50 (dd, J=8.98, 1.95 Hz, 1H), 7.84 (d, J=9.18 Hz, 1H), 8.44 (d, J=1.76 Hz, 1H). MS (ESI) (M+H)⁺: 342.05.

Step F. 1-(cyclohexylmethyl)-2-(1,1-dimethylpropyl)-1H-benzimidazol-5-amine

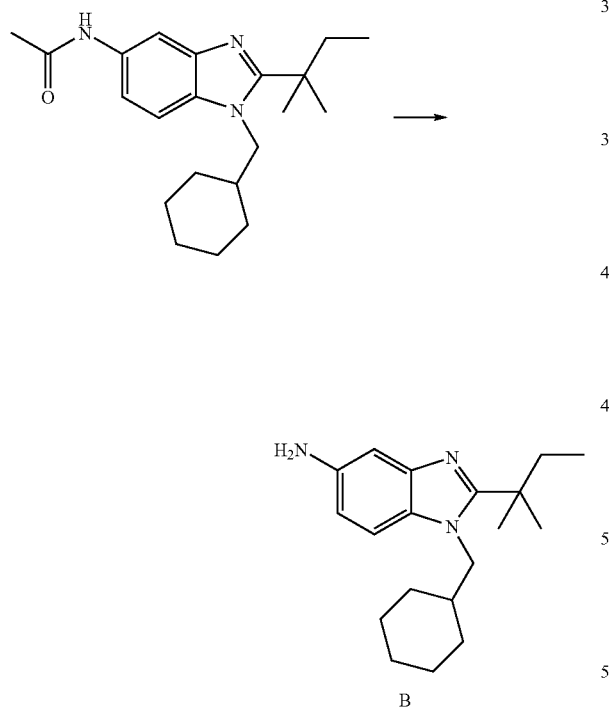

N-[1-(cyclohexylmethyl)-2-(1,1-dimethylpropyl)-1H-benzimidazol-5-yl]acetamide (110.0 mg, 0.32 mmol) was dissolved in EtOH (3 mL) and 2N HCl (2 mL) in a Teflon-capped test tube. The vessel was irradiated by microwave for 45 min. at 120° C. Upon evaporation of the solvent, the title compound was obtained as a grey white solid (117.8 mg, 100%). ¹H NMR (400 MHz, $CD_3OD$): δ 0.87 (t, J=7.52 Hz, 3H), 1.27 (m, 5H), 1.66 (m, 3H), 1.71 (s, 6H), 1.78 (m, 2H), 2.05 (q, J=7.42 Hz, 2H), 2.13 (m, 1H), 4.53 (d, J=7.62 Hz, 2H), 7.66 (dd, J=8.79, 1.56 Hz, 1H), 7.97 (d, J=1.76 Hz, 1H), 8.17 (d, J=8.79 Hz, 1H); MS (ESI) (M+H)⁺: 300.05.

Example 4

N-[2-tert-Butyl-1-(tetrahydro-2H-pyran-4-ylmethyl)-1H-benzimidazol-5-yl]-N-methylbutane-1-sulfonamide

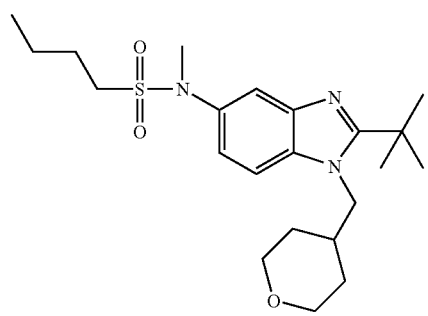 [SMILES: CCCCS(=O)(=O)N(C)c1ccc2c(c1)nc(C(C)(C)C)n2CC1CCOCC1]

Step A: N-[2-tert-Butyl-1-(tetrahydro-2H-pyran-4-ylmethyl)-1H-benzimidazol-5-yl]-N-methylbutane-1-sulfonamide

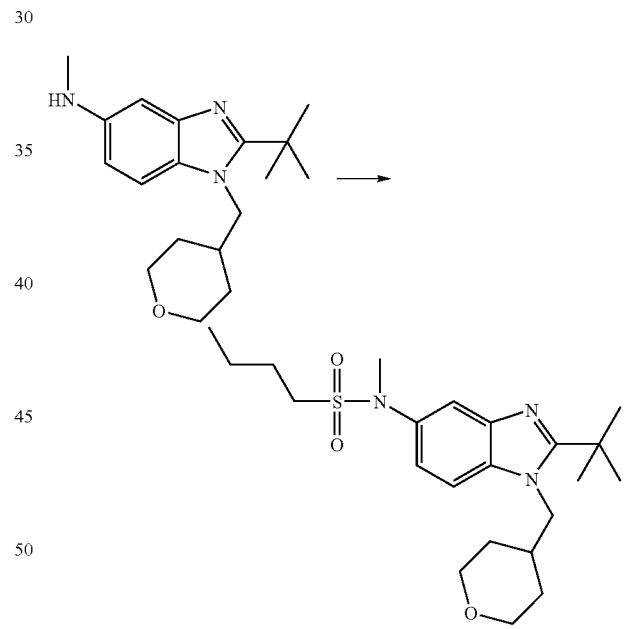

2-tert-Butyl-N-methyl-1-(tetrahydro-2H-pyran-4-ylmethyl)-1H-benzimidazol-5-amine (for preparation see following Steps B, C, D, E and F) (38 mg, 0.126 mmol) and 1-butanesulfonyl chloride (0.025 mL, 0.189 mmol) were stirred in 3 mL of DCM containing a catalytic amount of DMAP at rt overnight. The solvent was evaporated and the product was purified by reversed-phase HPLC using 10-60% $CH_3CN/H_2O$ and lyophilized affording the title compound as the corresponding TFA salt. Yield: 39 mg (58%). ¹H NMR (400 MHz, METHANOL-$D_4$): δ 0.88-0.94 (m, J=7.42, 7.42 Hz, 3H), 1.43 (dq, J=15.06, 7.41 Hz, 2H), 1.53-1.59 (m, 2H) 1.59-1.66 (m, 2H), 1.69 (s, 9H), 1.71-1.77 (m, 2H), 2.35-2.42 (m, 1H), 3.10-3.16 (m, 2H), 3.35 (dt, J=11.52, 2.73 Hz, 2H), 3.40 (s, 3H), 3.93 (d, J=3.12 Hz, 1H), 3.96 (d, J=3.71 Hz, 1H), 4.54 (d, J=7.42 Hz, 2H), 7.69 (dd, J=8.98, 2.15 Hz, 1H), 7.81 (d, J=1.56 Hz, 1H), 7.97 (d, J=8.98 Hz, 1H); MS (ESI) (M+H)$^+$422.2; Anal. Calcd for $C_{22}H_{35}N_3O_3S$+1.3 TFA+1.2 $H_2O$: C, 49.96; H, 6.60; N, 7.10. Found: C, 49.98; H, 6.67; N, 6.83.

Step B: Methyl (4-fluoro-3-nitrophenyl)carbamate

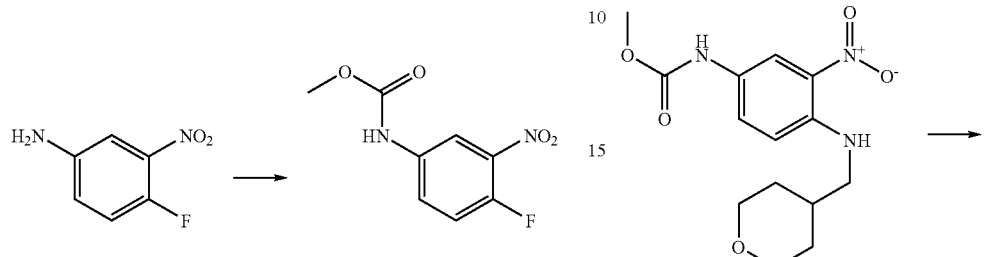

Methyl chloroformate (13.2 mL, 170.2 mmol) was added dropwise to a cold (0° C.) dichloromethane (200 mL) solution of 4-fluoro-3-nitro aniline (24.15 g, 154.7 mmol) and DIPEA (35 mL, 201 mmol). The reaction mixture was stirred at rt overnight. The solution was then diluted with 200 mL of dichloromethane and washed with 2M HCl, brine and dried over anhydrous $MgSO_4$. The solvent was concentrated and the product was directly used for next step without further purification. Yield: 35.5 g (99%). $^1$H NMR (400 MHz, CHLOROFORM-D): δ 3.81 (s, 3H), 7.02 (s, 1H), 7.23 (m, 1H), 7.72 (d, J=8.59 Hz, 1H), 8.17 (dd, J=6.35, 2.64 Hz, 1H).

Step C: Methyl {3-nitro-4-[(tetrahydro-2H-pyran-4-ylmethyl)amino]phenyl}carbamate

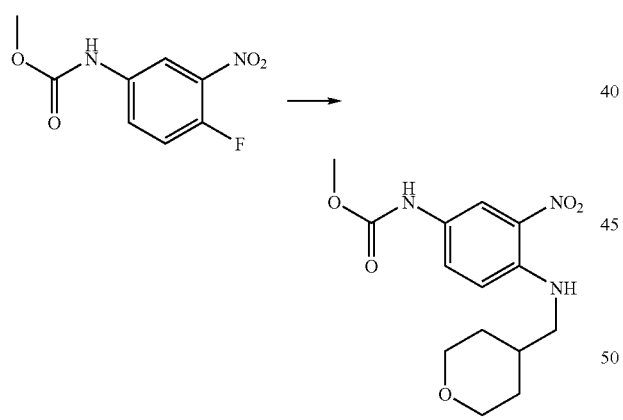

Methyl (4-fluoro-3-nitrophenyl)carbamate (2.0 g, 9.32 mmol) and 4-aminomethyl tetrahydropyran (1.28 g, 11.2 mmol) were stirred in 50 mL of EtOH containing TEA (2.0 mL, 14.0 mmol) at 75° C. for 48 h. The solvent was evaporated. The residue was dissolved in EtOAc and washed with aqueous 5% $KHSO_4$, saturated aqueous $NaHCO_3$ solution, brine and dried over anhydrous $MgSO_4$. The crude product was purified by silica gel flash chromatography using 1:1/hexanes:EtOAc as eluent. Yield: 2.53 g (88%). $^1$H NMR (400 MHz, CHLOROFORM-D): δ 1.42 (ddd, J=25.24, 12.06, 4.49 Hz, 2H), 1.73 (d, J=1.76 Hz, 1H), 1.76 (d, J=1.95 Hz, 1H), 1.88-2.01 (m, 1H), 3.22 (dd, J=6.74, 5.57 Hz, 2H), 3.42 (td, J=11.86, 2.05 Hz, 2H), 3.78 (s, 3H), 4.01 (d, J=4.30 Hz, 1H), 4.04 (d, J=3.51 Hz, 1H), 6.48 (br.s, 1H), 6.85 (d, J=9.37 Hz, 1H), 7.65 (br.s, 1H), 8.03-8.09 (m, 2H).

Step D: Methyl {3-amino-4-[(tetrahydro-2H-pyran-4-ylmethyl)amino]phenyl}carbamate

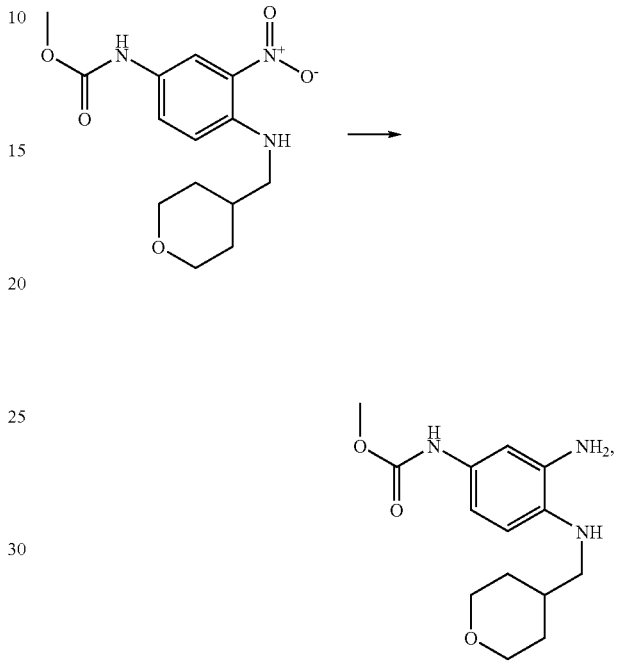

Methyl {3-nitro-4-[(tetrahydro-2H-pyran-4-ylmethyl)amino]phenyl}carbamate (2.53 g, 8.18 mmol) was dissolved in 50 mL of EtOAc containing a catalytic amount of 10% Pd/C. The solution was shaken under $H_2$ atmosphere (40 psi) using a Parr hydrogenation apparatus overnight at rt. The solution was filtered through celite and the solvent was evaporated. Yield: 2.29 g (99%). $^1$H NMR (400 MHz, CHLOROFORM-D): δ 1.40 (ddd, J=25.09, 12.01, 4.49 Hz, 2H), 1.70-1.74 (m, 1 H), 1.74-1.77 (m, 1H), 1.81-1.92 (m, 1H), 2.99 (d, J=6.64 Hz, 2H), 3.34 (br.s, 2 H), 3.41 (dt, J=11.81, 2.15 Hz, 2H), 3.74 (s, 3H), 3.99 (d, J=3.51 Hz, 1H), 4.02 (d, J=3.51 Hz, 1H), 6.38 (br.s, 1H), 6.55-6.60 (m, 1H), 6.62-6.68 (m, 1H), 6.95 (br.s, 1H).

Step E: Methyl [2-tert-butyl-1-(tetrahydro-2H-pyran-4-ylmethyl)-1H-benzimidazol-5-yl]carbamate

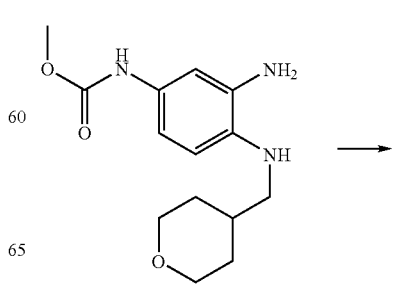

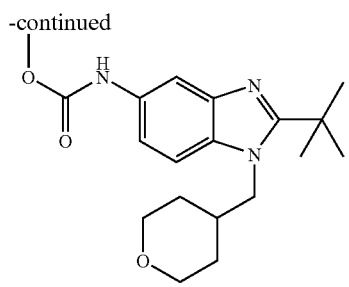

Methyl {3-amino-4-[(tetrahydro-2H-pyran-4-ylmethyl)amino]phenyl} carbamate (2.29 g, 8.20 mmol) and DMAP (0.20 g, 1.64 mmol) were dissolved in 75 mL of DCM. Trimethylacetyl chloride (1.10 mL, 9.02 mmol) was added dropwise and the solution was stirred at rt for 2 h. The solution was washed with aqueous NaHCO$_3$ solution, brine and dried over anhydrous MgSO$_4$. The residue was dissolved in 25 mL of AcOH and was heated at 125° C. for 1h using a Personal Chemistry microwave apparatus. The solvent was evaporated. The residue was dissolved in EtOAc and washed with aqueous NaHCO$_3$ solution, brine and dried over anhydrous MgSO$_4$. The crude product was purified by silica gel flash chromatography using 4:3/hexanes:acetone as eluent. Yield: 1.81 g (64%). $^1$H NMR (400 MHz, CHLOROFORM-D): δ 1.48-1.54 (m, 4H) 1.56 (s, 9H) 2.23-2.35 (m, 1H) 3.27-3.35 (m, 2H) 3.78 (s, 3H) 3.96 (t, J=2.93 Hz, 1H) 3.99 (t, J=3.03 Hz, 1H) 4.18 (d, J=7.42 Hz, 2H) 6.63 (br.s, 1H) 7.24-7.28 (m, 1H) 7.41 (br.s, 1H) 7.61 (d, J=1.95 Hz, 1H).

Step F: 2-tert-Butyl-N-methyl-1-(tetrahydro-2H-pyran-4-ylmethyl)-1H-benzimidazol-5-amine

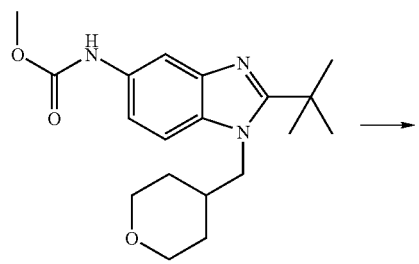

Methyl [2-tert-butyl-1-(tetrahydro-2H-pyran-4-ylmethyl)-1H-benzimidazol-5-yl]carbamate (1.80 g, 5.21 mmol) was dissolved in 75 mL of THF at 0° C. 1M HCl/ether (7.3 mL, 7.29 mmol) was added dropwise and the solution was stirred at 0° C. for 15 min. LiAlH$_4$ (988 mg, 26.1 mmol) was added slowly and the solution was stirred at rt overnight. The reaction was quenched at 0° C. by the addition of MeOH (5 mL) followed by water (10 mL) and the solution was left to stir at rt for 30 min. Anhydrous Na$_2$SO$_4$ (10 g) was added and the solution was stirred at rt for another 30 min. The solution was filtered and the solvent was evaporated. The residue was dissolved in EtOAc and washed with aqueous NaHCO$_3$ solution, brine and dried over anhydrous MgSO$_4$. The solvent was evaporated. Yield: 1.54 g (98%). $^1$H NMR (400 MHz, CHLOROFORM-D): δ 1.49-1.53 (m, 4H), 1.53-1.57 (m, 9H), 2.22-2.32 (m, 1H), 2.87 (s, 3H), 3.26-3.35 (m, 2H), 3.95 (t, J=3.03 Hz, 1H), 3.97-4.00 (m, 1H), 4.13 (d, J=7.42 Hz, 2H), 6.61 (dd, J=8.59, 2.15 Hz, 1H), 6.99 (d, J=1.95 Hz, 1H), 7.11 (d, J=8.59 Hz, 1H).

Example 5

N-[2-tert-Butyl-1-(tetrahydro-2H-pyran-4-ylmethyl)-1H-benzimidazol-5-yl]-N-methyl-2-pyrrolidin-1-ylethanesulfonamide

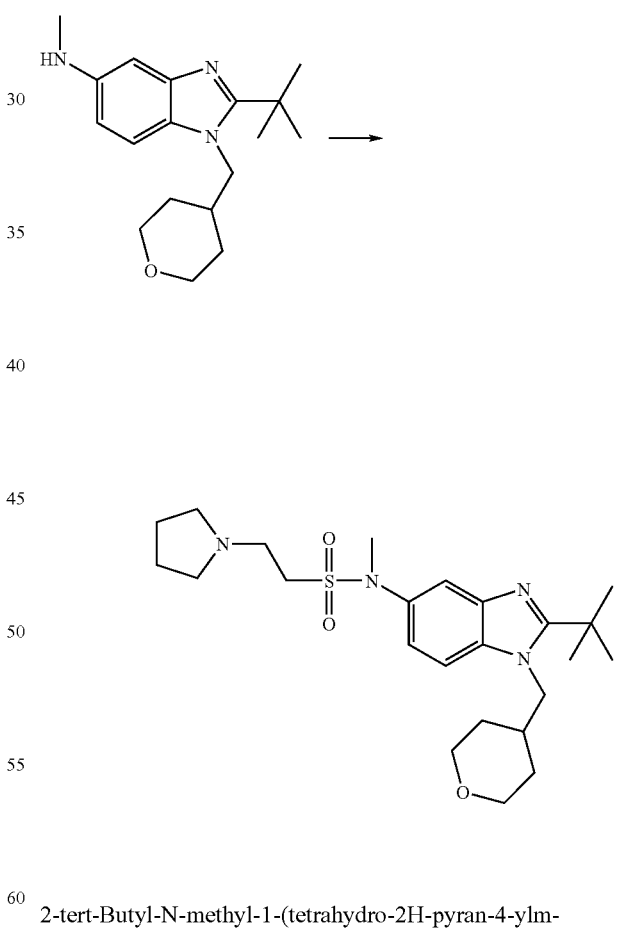

2-tert-Butyl-N-methyl-1-(tetrahydro-2H-pyran-4-ylmethyl)-1H-benzimidazol-5-amine (30 mg, 0.0996 mmol) was dissolved in 2 mL of DCE containing pyridine (0.012 mL, 0.149 mmol). 2-Chloro-1-ethanesulfonyl chloride (0.012 mL, 0.129 mmol) was added and the solution was stirred at rt for 3 h. Pyrrolidine (0.080 mL, 0.996 mmol) was added and the solution was stirred at rt for 3 h. The solution was washed with saturated aqueous NaHCO₃ solution, brine and dried over anhydrous MgSO₄. The product was purified by reversed-phase HPLC using 10-50% CH₃CN/H₂O and lyophilized affording the title compound as the corresponding TFA salt. Yield: 44 mg (77%). ¹H NMR (400 MHz, METHANOL-D₄): δ 1.50-1.56 (m, 2H), 1.56-1.64 (m, 2H), 1.68 (s, 9H), 2.00-2.08 (m, 2H), 2.09-2.20 (m, 2H), 2.32-2.43 (m, 1H), 3.06-3.21 (m, 2H), 3.35 (td, J=11.67, 2.25 Hz, 2H), 3.45 (s, 3H), 3.63-3.77 (m, 6H), 3.93 (d, J=3.12 Hz, 1H), 3.96 (d, J=3.12 Hz, 1H), 4.53 (d, J=7.62 Hz, 2H), 7.66 (dd, J=8.98, 1.95 Hz, 1H), 7.84 (d, J=1.56 Hz, 1H), 7.95 (d, J=8.98 Hz, 1H); MS (ESI) (M+H)⁺ 463.1.

Example 6

N-[2-tert-Butyl-1-(tetrahydro-2H-pyran-4-ylmethyl)-1H-benzimidazol-5-yl]-N-methyl-2-morpholin-4-ylethanesulfonamide

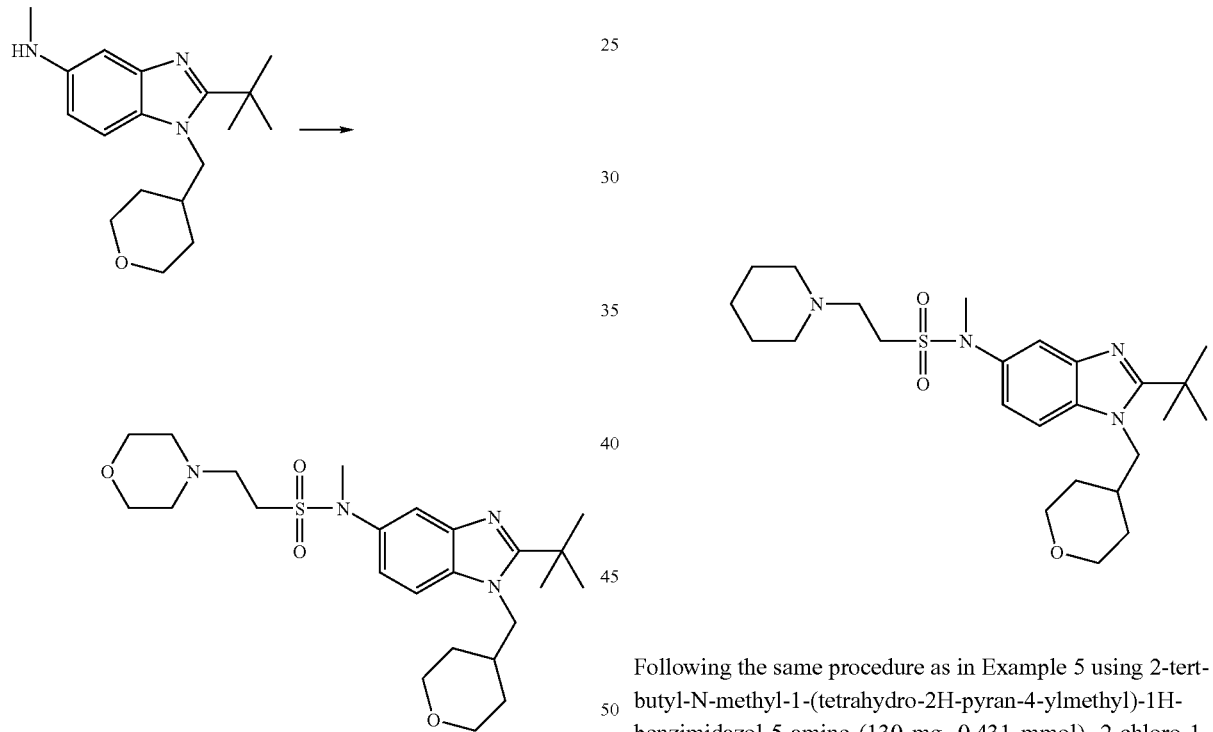

Following the same procedure as in Example 5 using 2-tert-butyl-N-methyl-1-(tetrahydro-2H-pyran-4-ylmethyl)-1H-benzimidazol-5-amine (36 mg, 0.119 mmol), 2-chloro-1-ethanesulfonyl chloride (0.015 mL, 0.143 mmol), pyridine (0.015 mL, 0.179 mmol) and morpholine (0.050 mL, 0.595 mmol) in 3 mL of DCE. The product was purified by reversed-phase HPLC using 10-50% CH₃CN/H₂O and lyophilized affording the title compound as the corresponding TFA salt. Yield: 42 mg (50%). ¹H NMR (400 MHz, METHANOL-D₄): δ 1.51-1.57 (m, 2H), 1.58-1.66 (m, 2H), 1.69 (s, 9H), 2.33-2.42 (m, 1H), 3.31-3.40 (m, 4H), 3.45 (s, 3H), 3.57-3.63 (m, 2H), 3.68-3.75 (m, 2H), 3.89 (br.s, 2H), 3.93 (d, J=3.51 Hz, 1H), 3.96 (d, J=2.34 Hz, 1H), 4.55 (d, J=7.62 Hz, 2H), 7.70 (dd, J=8.98, 1.95 Hz, 1H), 7.86 (d, J=2.15 Hz, 1H), 7.99 (d, J=8.98 Hz, 1H); MS (ESI) (M+H)⁺ 479.0; Anal. Calcd for C₂₄H₃₈N₄O₄S+2.5 TFA+1.0 H₂O: C, 44.56; H, 5.48; N, 7.17. Found: C, 44.53; H, 5.38; N, 7.26.

Example 7

N-[2-tert-Butyl-1-(tetrahydro-2H-pyran-4-ylmethyl)-1H-benzimidazol-5-yl]-N-methyl-2-piperidin-1-ylethanesulfonamide

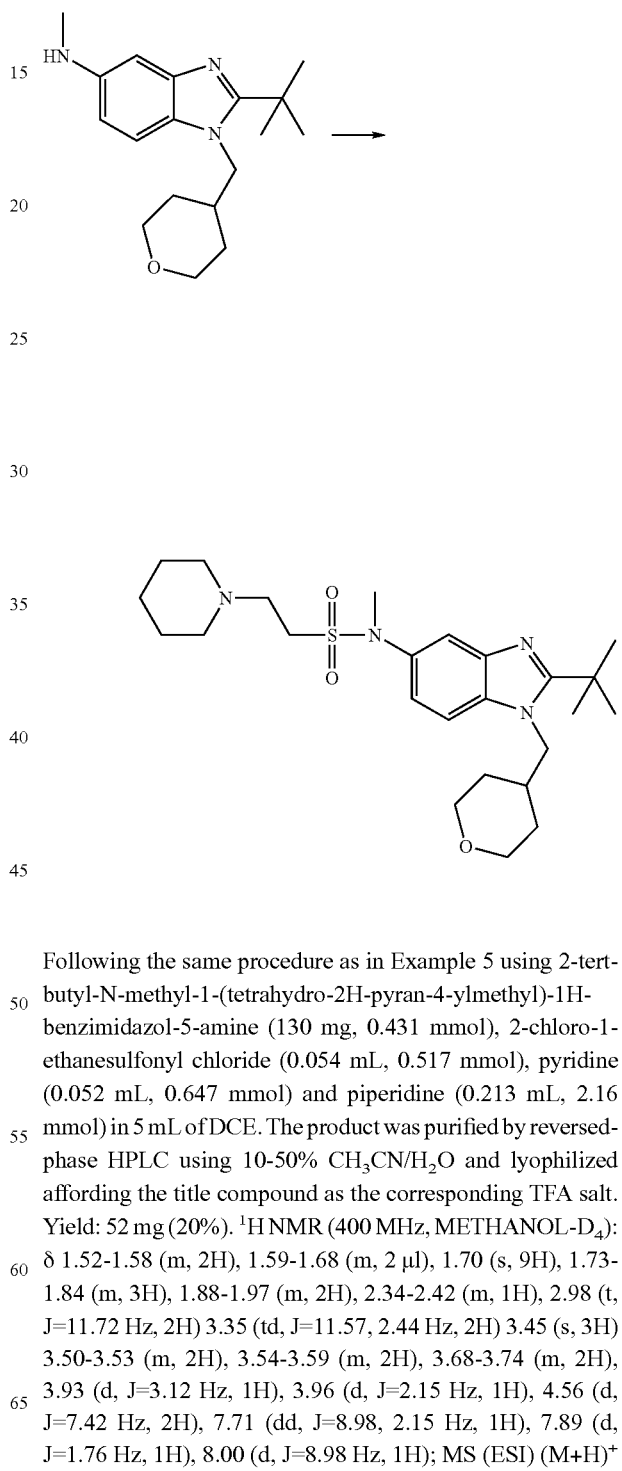

Following the same procedure as in Example 5 using 2-tert-butyl-N-methyl-1-(tetrahydro-2H-pyran-4-ylmethyl)-1H-benzimidazol-5-amine (130 mg, 0.431 mmol), 2-chloro-1-ethanesulfonyl chloride (0.054 mL, 0.517 mmol), pyridine (0.052 mL, 0.647 mmol) and piperidine (0.213 mL, 2.16 mmol) in 5 mL of DCE. The product was purified by reversed-phase HPLC using 10-50% CH₃CN/H₂O and lyophilized affording the title compound as the corresponding TFA salt. Yield: 52 mg (20%). ¹H NMR (400 MHz, METHANOL-D₄): δ 1.52-1.58 (m, 2H), 1.59-1.68 (m, 2 μl), 1.70 (s, 9H), 1.73-1.84 (m, 3H), 1.88-1.97 (m, 2H), 2.34-2.42 (m, 1H), 2.98 (t, J=11.72 Hz, 2H) 3.35 (td, J=11.57, 2.44 Hz, 2H) 3.45 (s, 3H) 3.50-3.53 (m, 2H), 3.54-3.59 (m, 2H), 3.68-3.74 (m, 2H), 3.93 (d, J=3.12 Hz, 1H), 3.96 (d, J=2.15 Hz, 1H), 4.56 (d, J=7.42 Hz, 2H), 7.71 (dd, J=8.98, 2.15 Hz, 1H), 7.89 (d, J=1.76 Hz, 1H), 8.00 (d, J=8.98 Hz, 1H); MS (ESI) (M+H)⁺

477.0; Anal. Calcd for $C_{25}H_{40}N_4O_3S+3.4$ TFA+0.9 $H_2O$: C, 43.38; H, 5.17; N, 6.36. Found: C, 43.41; H, 5.14; N, 6.36.

Example 8

N-[2-tert-Butyl-1-(tetrahydro-2H-pyran-4-ylmethyl)-1H-benzimidazol-5-yl]-2-methoxy-N-methylethanesulfonamide

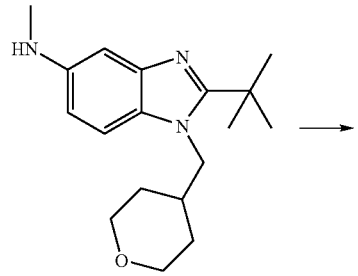

Following the same procedure as in Example 5 using 2-tert-butyl-N-methyl-1-(tetrahydro-2H-pyran-4-ylmethyl)-1H-benzimidazol-5-amine (60 mg, 0.199 mmol), 2-chloro-1-ethanesulfonyl chloride (0.024 mL, 0.299 mmol), pyridine (0.024 mL, 0.299 mmol) and 2M NaOMe/MeOH (0.5 mL) in 3 mL of DCE. The solvent was evaporated. The residue was dissolved in EtOAc and washed with saturated aqueous NaHCO$_3$ solution, brine and dried over anhydrous MgSO$_4$. The product was purified by reversed-phase HPLC using 10-50% CH$_3$CN/H$_2$O and lyophilized affording the title compound as the corresponding TFA salt. Yield: 20 mg (20%). $^1$H NMR (400 MHz, METHANOL-D$_4$): δ 1.52-1.57 (m, 2H), 1.57-1.63 (m, 2H), 1.67 (s, 9H), 2.35-2.41 (m, 1H), 3.32-3.35 (m, 4H), 3.36 (s, 3H), 3.38 (s, 3H), 3.75 (t, J=5.57 Hz, 2H), 3.93 (d, J=3.51 Hz, 1H), 3.95 (d, J=3.71 Hz, 1H), 4.52 (d, J=7.62 Hz, 2H), 7.66 (dd, J=8.98, 2.15 Hz, 1H), 7.83 (d, J=1.95 Hz, 1H), 7.92 (d, J=9.18 Hz, 1H); MS (ESI) (M+H)$^+$ 424.0; Anal. Calcd for $C_{21}H_{33}N_3O_4S+1.2$ TFA+0.9 $H_2O$: C, 48.74; H, 6.29; N, 7.29. Found: C, 48.69; H, 6.19; N, 7.50.

Example 9

Product A: N-[2-tert-Butyl-1-(tetrahydro-2H-pyran-4-ylmethyl)-1H-benzimidazol-5-yl]-2-[(2-hydroxyethyl)amino]-N-methylethanesulfonamide Product B: 2-(2-Aminoethoxy)-N-[2-tert-butyl-1-(tetrahydro-2H-pyran-4-ylmethyl)-1H-benzimidazol-5-yl]-N-methylethanesulfonamide

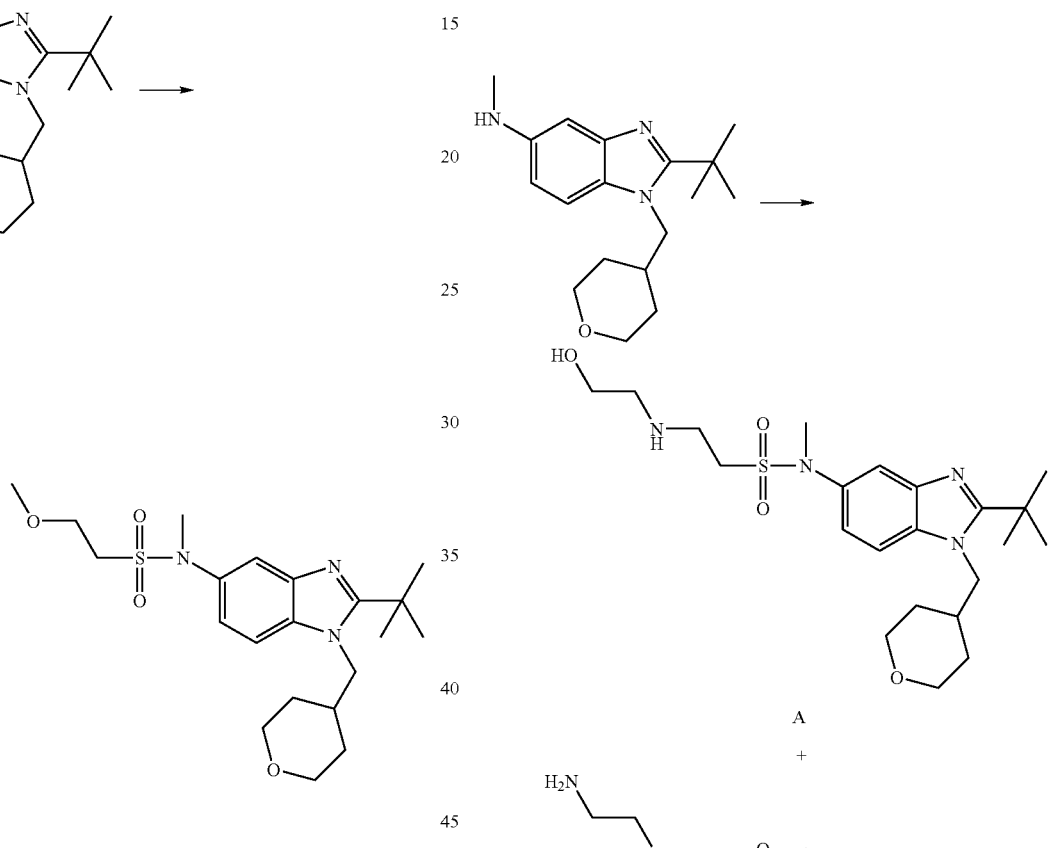

Following the same procedure as in Example 5 using 2-tert-butyl-N-methyl-1-(tetrahydro-2H-pyran-4-ylmethyl)-1H-benzimidazol-5-amine (33 mg, 0.109 mmol), 2-chloro-1-ethanesulfonyl chloride (0.014 mL, 0.131 mmol), pyridine (0.013 mL, 0.164 mmol) and ethanolamine (0.066 mL, 1.09 mmol) in 3 mL of DCE. The product was purified by reversed-phase HPLC using 10-50% CH$_3$CN/H$_2$O and lyophilized affording the title compounds as the corresponding TFA salts.

Yield: Product A: 37 mg (60%); Product B: 14 mg (23%). Product A: $^1$H NMR. (400 MHz, METHANOL-D$_4$): δ 1.51-1.57 (m, 2H), 1.56-1.63 (m, 2H), 1.68 (s, 9H), 2.33-2.42 (m, 1H), 3.16-3.21 (m, 2H), 3.35 (td, J=11.57, 2.44 Hz, 2H), 3.45 (s, 3H), 3.49-3.55 (m, 2H), 3.59-3.64 (m, 2H), 3.75-3.80 (m, 2H), 3.93 (d, J=3.12 Hz, 1H), 3.96 (d, J=2.73 Hz, 1H), 4.54 (d, J=7.62 Hz, 2H), 7.68 (dd, J=8.98, 1.95 Hz, 1H), 7.85 (d, J=1.56 Hz, 1H), 7.97 (d, J=8.79 Hz, 1H); MS (ESI) (M+H)$^+$ 453.0; Anal. Calcd for C$_{22}$H$_{36}$N$_4$O$_4$S+2.6 TFA+1.5 H$_2$O: C, 42.10; H, 5.40; N, 7.22. Found: C, 42.02; H, 5.25; N, 7.41. Product B: $^1$H NMR (400 MHz, METHANOL-D$_4$): δ 1.50-1.56 (m, 2 H), 1.55-1.64 (m, 2H), 1.66 (s, 9H), 2.33-2.41 (m, 1H), 3.07 (s, 3H), 3.18 (t, J=5.66 Hz, 2H), 3.31-3.40 (m, 4H), 3.62 (t, J=5.57 Hz, 2H), 3.90-3.97 (m, 4H), 4.47 (d, J=7.62 Hz, 2H), 6.90 (d, J=2.34 Hz, 1H), 7.16 (dd, J=9.37, 2.34 Hz, 1H), 7.75 (d, J=9.37 Hz, 1H); MS (ESI) (M+H)$^+$ 453.0; Anal. Calcd for C$_{22}$H$_{36}$N$_4$O$_4$S+1.5 TFA: C, 48.15; H, 6.06; N, 8.97. Found: C, 48.34; H, 6.22; N, 8.57.

Example 10

N-[2-tert-Butyl-1-(tetrahydro-2H-pyran-4-ylmethyl)-1H-benzimidazol-5-yl]-N-methylethylenesulfonamide

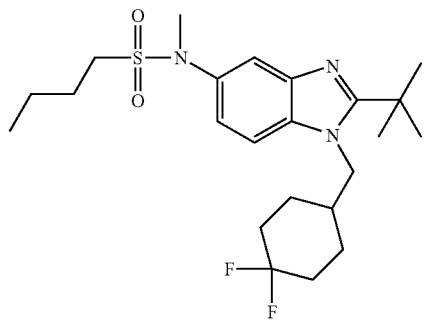 [SMILES: CCCCS(=O)(=O)N(C)c1ccc2c(c1)nc(C(C)(C)C)n2CC1CCC(F)(F)CC1]

Following the same procedure as in Example 5 using 2-tert-butyl-N-methyl-1-(tetrahydro-2H-pyran-4-ylmethyl)-1H-benzimidazol-5-amine (49 mg, 0.163 mmol), 2-chloro-1-ethanesulfonyl chloride (0.022 mL, 0.212 mmol), pyridine (0.020 mL, 0.245 mmol) and 2M ammonia/EtOH (0.5 mL) in 3 mL of DCE. The solvent was evaporated. The residue was dissolved in EtOAc and washed with saturated aqueous NaHCO$_3$ solution, brine and dried over anhydrous MgSO$_4$. The product was purified by reversed-phase HPLC using 10-60% CH$_3$CN/H$_2$O and lyophilized affording the title compound as the corresponding TFA salt. Yield: 34 mg (41%). $^1$H NMR (400 MHz, METHANOL-D$_4$): δ 1.52-1.58 (m, 2H), 1.58-1.67 (m, 2H), 1.69 (s, 9H), 2.34-2.43 (m, 1H), 3.32 (s, 3H), 3.33-3.39 (m, 2H), 3.93 (d, J=3.12 Hz, 1H), 3.95 (d, J=3.52 Hz, 1H), 4.55 (d, J=7.42 Hz, 2H), 6.10 (d, J=8.79 Hz, 1H), 6.13 (d, J=2.15 Hz, 1H), 6.70 (dd, J=16.50, 10.06 Hz, 1H), 7.61 (dd, J=8.98, 2.15 Hz, 1H), 7.76 (d, J=1.56 Hz, 1H), 7.96 (d, J=8.98 Hz, 1H); MS (ESI) (M+H)$^+$ 392.0; Anal. Calcd for C$_{20}$H$_{29}$N$_3$O$_3$S+1.3 TFA+0.3 H$_2$O: C, 49.79; H, 5.71; N, 7.71. Found: C, 49.81; H, 5.77; N, 7.74.

Example 11

N-{2-tert-Butyl-1-[(4,4-difluorocyclohexyl)methyl]-1H-benzimidazol-5-yl}-N-methylbutane-1-sulfonamide

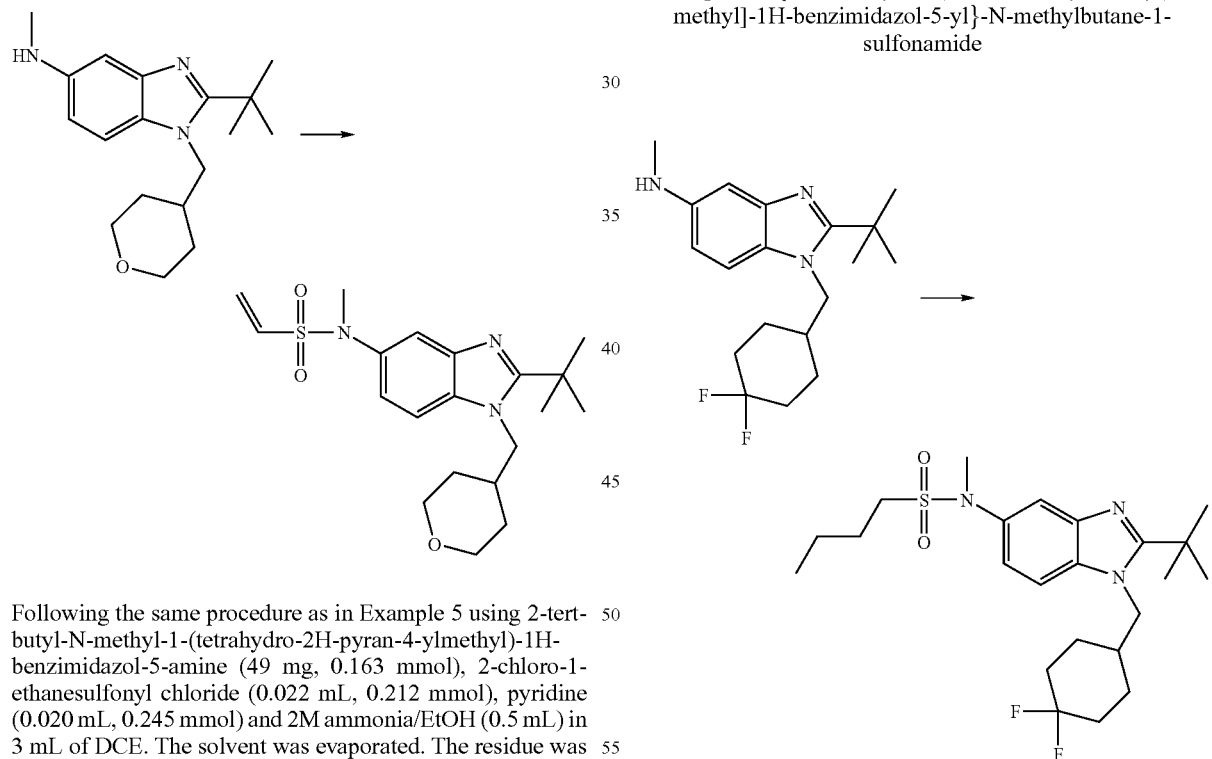

Step A: N-{2-tert-Butyl-1-[(4,4-difluorocyclohexyl)methyl]-1H-benzimidazol-5-yl}-N-methylbutane-1-sulfonamide 2-tert-Butyl-1-[(4,4-difluorocyclohexyl)methyl]-N-methyl-1H-benzimidazol-5-amine (for preparation see following Steps B, C, D, E, F and G) (46 mg, 0.137 mmol) and 1-butanesulfonyl chloride (0.063 mL, 0.411 mmol) were stirred in 3 mL of DCM containing a catalytic amount of DMAP at it for 6 h. The solvent was evaporated and the product was purified by reversed-phase HPLC using 10-75% CH$_3$CN/H$_2$O and lyophilized affording the title compound as the corresponding TFA salt. Yield: 48 mg (62%). $^1$H NMR (400 MHz, METHANOL-D$_4$): δ 0.92 (t, J=7.32 Hz, 3H), 1.43 (td, J=14:94, 7.42 Hz, 2H), 1.52-1.63 (m, 2H), 1.69 (s, 9H), 1.70-1.76 (m, 4H), 1.76-1.84 (m, 2H), 2.02-2.12 (m, 2H), 2.22-2.31 (m, 1H), 3.10-3.17 (m, 2H), 3.41 (s, 3H), 4.56 (d, J=7.62 Hz, 2H), 7.69 (dd, J=8.98, 2.15 Hz, 1H), 7.82 (d, J=1.76 Hz, 1H), 7.96 (d, J=9.18 Hz, 1H); MS (ESI) (M+H)+ 456.

Step B: tert-Butyl [(4,4-difluorocyclohexyl)methyl]carbamate

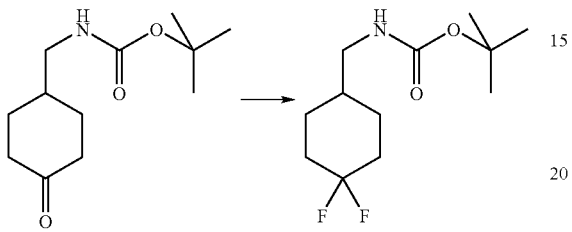

4-N-Boc-aminomethyl cyclohexanone (1.00 g, 4.4 mmol) was dissolved in 30 mL of DCM at 0° C. DAST (1.45 mL, 11.0 mmol) was added dropwise and the solution was stirred at rt overnight. The solution was washed with aqueous 5% KHSO₄ solution, saturated aqueous NaHCO₃ solution, brine and dried over anhydrous MgSO₄. The crude product was purified by silica gel flash chromatography using 3:1/hexanes:EtOAc as eluent. Yield: 508 mg (46%). ¹H NMR (400 MHz, CHLOROFORM-D): δ 1.19-1.36 (m, 2H), 1.44 (s, 9H), 1.51-1.56 (m, 1H), 1.59-1.75 (m, 2H), 1.75-1.84 (m, 2H), 2.01-2.16 (m, 2H), 3.03 (t, J=6.54 Hz, 2H), 4.62 (br.s, 1H).

Step C: [(4,4-Difluorocyclohexyl)methyl]amine hydrochloride

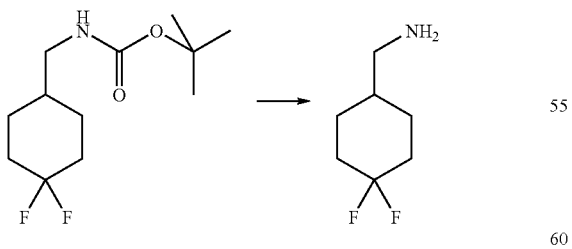

tert-Butyl [(4,4-difluorocyclohexyl)methyl]carbamate (505 mg, 2.03 mmol) was stirred in 5 mL of 1M HCl/AcOH at rt for 2 h. The solvent was evaporated. The residue was washed with ether, filtered and dried. Yield: 330 mg (88%). ¹H NMR (400 MHz, METHANOL-D₄): δ 1.28-1.40 (m, 2H), 1.71-1.82 (m, 2H), 1.84 (d, J=3.12 Hz, 2H), 1.86-1.89 (m, 1H), 2.03-2.15 (m, 2H), 2.85 (d, J=7.03 Hz, 2H).

Step D: Methyl (4-{[(4,4-difluorocyclohexyl)methyl]amino}-3-nitrophenyl)carbamate Following the same procedure as in Step C of Example 4 using [(4,4-difluorocyclohexyl)methyl]amine hydrochloride (210 mg, 1.12 mmol), methyl (4-fluoro-3-nitrophenyl)carbamate (200 mg, 0.934 mmol) and TEA (0.390 mL, 2.80 mmol) in 10 mL of EtOH. The crude product was purified by silica gel flash chromatography using 5% ether/DCM as eluent. Yield: 200 mg (62%). ¹H NMR (400 MHz, CHLOROFORM-D): δ 1.34-1.47 (m, 2H), 1.65-1.75 (m, 2H), 1.78-1.85 (m, 1H), 1.90-1.93 (m, 1H), 1.94-1.97 (m, 1H), 2.10-2.21 (m, 2H), 3.23 (dd, J=6.64, 5.66 Hz, 2H), 3.78 (s, 3H), 6.48 (br.s, 1H), 6.83 (d, J=9.18 Hz, 1H), 7.66 (br.s, 1H), 8.05 (br.s, 1H), 8.07 (d, J=2.54 Hz, 1H).

Step E: Methyl (3-amino-4-{[(4,4-difluorocyclohexyl)methyl]amino}phenyl)carbamate Following the same procedure as in Step D of Example 4 using methyl (4-{[(4,4-difluorocyclohexyl)methyl]amino}-3-nitrophenyl)carbamate (200 mg, 0.583 mmol) and a catalytic amount of 10% Pd/C in 20 mL of EtOAc. Yield: 185 mg (99%). MS (ESI) (M+H)+ 314.29.

Step F: Methyl {2-tert-butyl-1-[(4,4-difluorocyclohexyl)methyl]-1H-benzimidazol-5-yl}carbamate

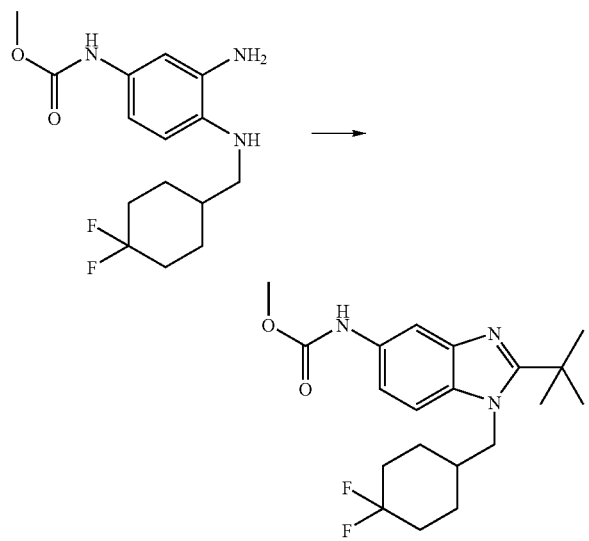

Methyl (3-amino-4-{[(4,4-difluorocyclohexyl)methyl]amino}phenyl)carbamate (185 mg, 0.590 mmol) and DMAP (15 mg, 0.118 mmol) were dissolved in 10 mL of DCM. Trimethylacetyl chloride (0.080 mL, 0.649 mmol) was added dropwise and the solution was stirred at rt for 2 h. The solution was washed with aqueous NaHCO₃ solution, brine and dried over anhydrous MgSO₄. The solvent was concentrated. The residue was dissolved in 4 mL of DCE and P₂O₅ (catalytic) was added and the solution was heated at 125° C. for 1 h using a Personal Chemistry microwave apparatus. The solution was washed with aqueous NaHCO₃ solution, brine and dried over anhydrous MgSO₄. The crude product was purified by silica gel flash chromatography using 50 to 75% EtOAc/hexanes. Yield: 122 mg (54%); ¹H NMR (400 MHz, CHLOROFORM-D): δ 1.43-1.52 (m, 2H), 1.55 (s, 9H), 1.57-1.66 (m, 2H), 1.67-1.74 (m, 2H), 2.08-2.18 (m, 3H), 3.79 (s, 3H), 4.19 (d, J=7.42 Hz, 2H), 6.63 (br.s, 1H), 7.23 (d, J=8.79 Hz, 1H), 7.37-7.46 (m, 1H), 7.62 (d, J=1.76 Hz, 1H).

Step G: 2-tert-Butyl-1-[(4,4-difluorocyclohexyl)methyl]-N-methyl-1H-benzimidazol-5-amine

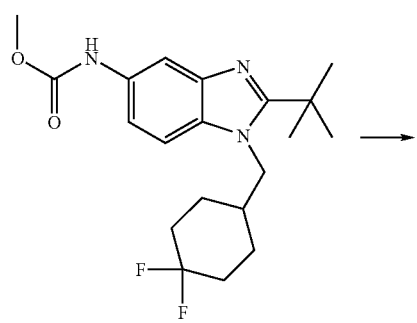

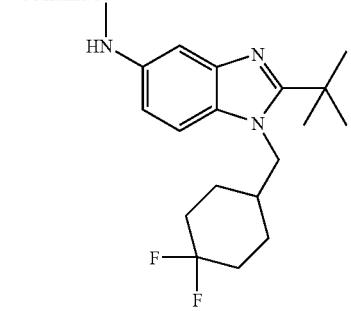

Methyl {2-tert-butyl-1-[(4,4-difluorocyclohexyl)methyl]-1H-benzimidazol-5-yl}carbamate (115 mg, 0.303 mmol) was dissolved in 10 mL of THF at 0° C. 1M Ha/ether (0.425 mL, 0.424 mmol) was added and the solution was stirred at 0° C. for 15 min. LiAlH₄ (57 mg, 1.52 mmol) was added slowly and the solution was stirred at rt overnight. The reaction was quenched at 0° C. by the addition of MeOH (1 mL) and water (2 mL). Anhydrous Na₂SO₄ (5.0 g) was added and the solution was stirred at rt for 30 min. The solution was filtered and the solvent was evaporated. The residue was dissolved in EtOAc and washed with saturated aqueous NaHCO₃ solution, brine and dried over anhydrous MgSO₄. Yield: 95 mg (93%). ¹H NMR (400 MHz, CHLOROFORM-D): δ 1.41-1.51 (m, 2H), 1.54 (s, 9H), 1.57-1.67 (m, 2H), 1.68-1.76 (m, 3H), 2.07-2.17 (m, 3H), 2.87 (s, 3H), 4.15 (d, J=7.42 Hz, 2H), 6.61 (dd, J=8.59, 2.34 Hz, 1H), 7.01 (d, J=1.95 Hz, 1H), 7.09 (d, J=8.59 Hz, 1H).

Example 12

N-{2-tert-Butyl-1-[(4,4-difluorocyclohexyl)methyl]-1H-benzimidazol-5-yl}-N-methyl-2-piperidin-1-ylethanesulfonamide

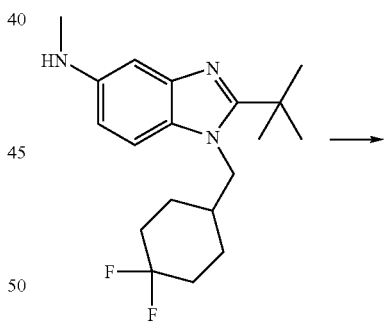

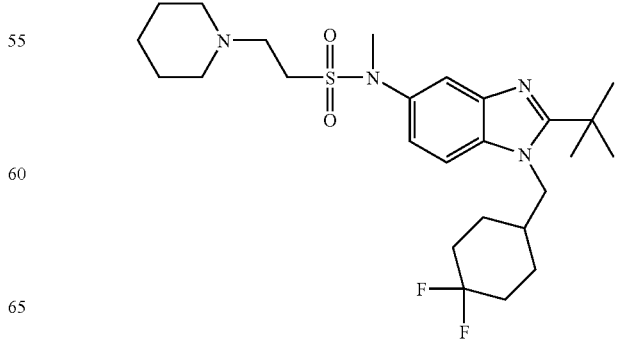

2-tert-Butyl-1-[(4,4-difluorocyclohexyl)methyl]-N-methyl-1H-benzimidazol-5-amine (45 mg, 0.134 mmol) and pyridine (0.022 mL, 0.268 mmol) were dissolved in 3 mL of DCE. 2-Chloro-1-ethanesulfonyl chloride (0.021 mL, 0.201 mmol) was added and the solution was stirred at rt for 2 h. Piperidine (0.066 mL, 0.670 mmol) was added and the solution was stirred at 75° C. for 2 h. The solution was washed with saturated aqueous $NaHCO_3$ solution, brine and dried over anhydrous $MgSO_4$. The product was purified by reversed-phase HPLC using 10-50% $CH_3CN/H_2O$ and lyophilized affording the title compound as the corresponding TFA salt. Yield: 40 mg (48%). $^1H$ NMR (400 MHz, METHANOL-$D_4$): δ 1.53-1.63 (m, 3H), 1.68 (s, 9H), 1.71-1.77 (m, 4H), 1.77-1.85 (m, 3H), 1.90-1.97 (m, 2H), 2.03-2.12 (m, 2H), 2.20-2.30 (m, 1H), 2.94-3.04 (m, 2H), 3.45 (s, 3H), 3.51-3.59 (m, 4H), 3.67-3.73 (m, 2 H), 4.55 (d, J=7.62 Hz, 2H), 7.68 (dd, J=8.98, 2.15 Hz, 1H), 7.86 (d, J=1.95 Hz, 1H), 7.95 (d, J=8.98 Hz, 1H); MS (ESI) (M+H)$^+$ 511.0; Anal. Calcd for $C_{25}H_{40}N_4O_2SF_2$+2.7 TFA+1.0 $H_2O$: C, 45.08; H, 5.39; N, 6.70. Found: C, 45.01; H, 5.32; N, 7.00.

What is claimed is:

1. A compound of Formula I or a pharmaceutically acceptable salt thereof:

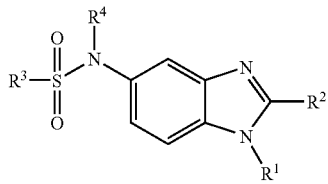

I wherein $R^1$ is selected from $C_{1-6}$alkyl, $C_{2-6}$alkenyl, phenyl-$C_{1-4}$alkyl, $C_{3-10}$cycloalkyl-$C_{1-4}$alkyl, $C_{4-6}$cycloalkenyl-$C_{1-4}$alkyl, $C_{6-10}$aryl, $C_{3-10}$cycloalkyl, $C_{3-6}$heterocycloalkyl-$C_{1-4}$alkyl, and $C_{4-6}$cycloalkenyl, wherein said $C_{1-6}$alkyl, $C_{2-6}$alkenyl, phenyl-$C_{1-4}$alkyl, $C_{3-10}$cycloalkyl-$C_{1-4}$alkyl, $C_{4-6}$cycloalkenyl-$C_{1-4}$alkyl, $C_{6-10}$aryl, $C_{3-10}$cycloalkyl, $C_{3-6}$heterocycloalkyl-$C_{1-4}$alkyl, and $C_{4-6}$cycloalkenyl used in defining $R^1$ is optionally substituted by one or more groups selected from halogen, methoxy, ethoxy, methyl, ethyl, hydroxy, and —$NR^5R^6$;

$R^2$ is selected from $C_{1-6}$alkyl, $C_{2-6}$alkenyl, $C_{3-6}$cycloalkyl and $C_{3-6}$cycloalkyl-$C_{1-4}$alkyl, wherein said $C_{1-6}$alkyl, $C_{2-6}$alkenyl, $C_{3-6}$cycloalkyl and $C_{3-6}$cycloalkyl-$C_{1-4}$alkyl used in defining $R^2$ is optionally substituted by one or more groups selected from halogen, methoxy, ethoxy, methyl, ethyl, hydroxy and —$NR^5R^6$;

$R^3$ is selected from $C_{2-6}$alkyl, $C_{3-6}$heterocycloalkyl and

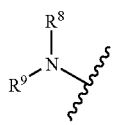

optionally subsitituted with one or more $C_{1-6}$alkyl, and; wherein said $C_{3-6}$heterocycloalkyl contain at least one nitrogen ring atom and the radical of $C_{3-6}$heterocycloalkyl is located on the at least one nitrogen ring atom, and wherein each of $R^8$ and $R^9$ is independently selected from —H, $C_{1-6}$alkyl, morpholinyl-$C_{1-3}$alkyl, pyrrolidinyl-$C_{1-3}$alkyl, and piperidinyl-$C_{1-3}$alkyl, wherein said $C_{1-6}$alkyl, morpholinyl-$C_{1-3}$alkyl, pyrrolidinyl-$C_{1-3}$alkyl, and piperidinyl-$C_{1-3}$alkyl are optionally substituted by one or more groups selected from halogen, methoxy, ethoxy, methyl, ethyl, hydroxy and —$NR^5R^6$;

$R^4$, $R^5$ and $R^6$ are independently selected from —H and $C_{1-3}$alkyl; and the compound is not:
N-[2-tert-Butyl-1-(cyclohexylmethyl)-1H-benzimidazol-5-yl]-N,N',N'-trimethylsulfamide;
N-[2-tert-Butyl-1-(cyclohexylmethyl)-1H-benzimidazol-5-yl]-N',N'-diethyl-N-methylsulfamide;
N'-[1-(cyclohexylmethyl)-2-(1,1-dimethylpropyl)-1H-benzimidazol-5-yl]-N,N-dimethyl-sulfamide;
N-[2-tert-Butyl-1-(tetrahydro-2H-pyran-4-ylmethyl)-1H-benzimidazol-5-yl]-N-methylbutane-1-sulfonamide;
N-[2-tert-Butyl-1-(tetrahydro-2H-pyran-4-ylmethyl)-1H-benzimidazol-5-yl]-N-methyl-2-pyrrolidin-1-ylethanesulfonamide;
N-[2-tert-Butyl-1-(tetrahydro-2H-pyran-4-ylmethyl)-1H-benzimidazol-5-yl]-N-methyl-2-morpholin-4-ylethanesulfonamide;
N-[2-tert-Butyl-1-(tetrahydro-2H-pyran-4-ylmethyl)-1H-benzimidazol-5-yl]-N-methyl-2-piperidin-1-ylethanesulfonamide;
N-[2-tert-Butyl-1-(tetrahydro-2H-pyran-4-ylmethyl)-1H-benzimidazol-5-yl]-2-methoxy-N-methylethanesulfonamide;
N-[2-tert-Butyl-1-(tetrahydro-2H-pyran-4-ylmethyl)-1H-benzimidazol-5-yl]-2-[(2-hydroxyethyl)amino]-N-methylethanesulfonamide;
2-(2-Aminoethoxy)-N-[2-tert-butyl-1-(tetrahydro-2H-pyran-4-ylmethyl)-1H-benzimidazol-5-yl]-N-methyl-ethanesulfonamide;
N-[2-tert-Butyl-1-(tetrahydro-2H-pyran-4-ylmethyl)-1H-benzimidazol-5-yl]-N-methylethylenesulfonamide;
N-{2-tert-Butyl-1-[(4,4-difluorocyclohexyl)methyl]-1H-benzimidazol-5-yl}-N-methylbutane-1-sulfonamide;
N-{2-tert-Butyl-1-[(4,4-difluorocyclohexyl)methyl]-1H-benzimidazol-5-yl}-N-methyl-2-piperidin-1-ylethanesulfonamide or pharmaceutically acceptable salts thereof.

2. A compound of Formula I or a pharmaceutically acceptable salt thereof:

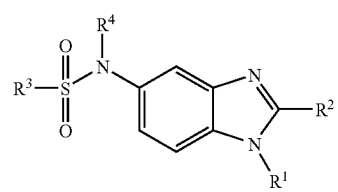

I wherein
$R^1$ is selected from cyclohexylmethyl, cyclopentylmethyl, cyclobutylmethyl, cyclopropylmethyl, 4,4-difluorocyclohexanemethyl, cyclohexylethyl, cyclopentylethyl, tetrahydropyranylmethyl, tetrahydrofuranylmethyl, 1-piperidinylethyl, N-methyl-2-piperidinyl-methyl and benzyl;

$R^2$ is selected from t-butyl, n-butyl, 2-methyl-2-butyl, isopentyl, 2-methoxy-2-propyl, 2-hydroxy-propyl, trifluoromethyl, 1,1-difluoroethyl, 2,2,2-trifluoroethyl, 1-cyclopropyl-ethyl, 1-methyl-propyl, 1,1-dimethyl-propyl, 1,1-dimethyl-3-buten-1-yl, ethyl, and 2-propyl;

$R^3$ is $C_{2-5}$alkyl and $R^8R^9N-$, wherein $R^8$ and $R^9$ are independently selected from —H, and $C_{1-3}$alkyl;

$R^4$ is selected from —H, $C_{1-10}$alkyl, $C_{2-10}$alkenyl, $C_{2-10}$alkynyl, $C_{3-10}$cycloalkyl, $C_{3-10}$cycloalkyl-$C_{1-6}$alkyl, and $C_{4-8}$cycloalkenyl-$C_{1-6}$alkyl; and the compound is not:

- N-[2-tert-Butyl-1-(cyclohexylmethyl)-1H-benzimidazol-5-yl]-N,N',N'-trimethylsulfamide;
- N-[2-tert-Butyl-1-(cyclohexylmethyl)-1H-benzimidazol-5-yl]-N',N'-diethyl-N-methylsulfamide;
- N-[1-(cyclohexylmethyl)-2-(1,1-dimethylpropyl)-1H-benzimidazol-5-yl]-N,N-dimethyl-sulfamide;
- N-[2-tert-Butyl-1-(tetrahydro-2H-pyran-4-ylmethyl)-1H-benzimidazol-5-yl]-N-methylbutane-1-sulfonamide;
- N[2-tert-Butyl-1-(tetrahydro-2H-pyran-4-ylmethyl)-1H-benzimidazol-5-yl]-N-methyl-2-pyrrolidin-1-ylethanesulfonamide;
- N-[2-tert-Butyl-1-tetrahydro-2H-s an-4-ylmethyl)-1H-benzimidazol-5-yl]-N-methyl-2-morpholin-4-ylethanesulfonamide;
- N-[2-tert-Butyl-1-(tetrahydro-2H-pyran-4-ylmethyl)-1H-benzimidazol-5-yl]-N-methyl-2-piperidin-1-ylethanesulfonamide;
- N-[2-tert-Butyl-1-(tetrahydro-2H-pyran-4-ylmethyl)-1H-benzimidazol-5-yl]-2-methoxy-N-methylethanesulfonamide;
- N-[2-tert-Butyl-1-(tetrahydro-2H-pyran-4-ylmethyl)-1H-benzimidazol-5-yl]-2-[(2-hydroxyethyl)amino]-N-methylethanesulfonamide;
- 2-(2-Aminoethoxy)-N-[2-tert-butyl-1-(tetrahydro-2H-pyran-4-ylmethyl)-1H-benzimidazol-5-yl]-N-methylethanesulfonamide;
- N-[2-tert-Butyl-1-(tetrahydro-2H-pyran-4-ylmethyl)-1H-benzimidazol-5-yl]-N-methylethylenesulfonamide;
- N-{2-tert-Butyl-1-[(4,4-difluorocyclohexyl)methyl]-1H-benzimidazol-5-yl}-N-methylbutane-1-sulfonamide;
- N-{2-tert-Butyl-1-[(4,4-difluorocyclohexyl)methyl]-1H-benzimidazol-5-yl}-N-methyl-2-piperidin-1-ylethanesulfonamide or pharmaceutically acceptable salts thereof.

3. A pharmaceutical composition comprising a compound according to claim 1 and a pharmaceutically acceptable carrier.

4. A pharmaceutical composition comprising a compound according to claim 2 and a pharmaceutically acceptable carrier.

* * * * *

UNITED STATES PATENT AND TRADEMARK OFFICE
CERTIFICATE OF CORRECTION

PATENT NO.       : 8,633,235 B2                                                                 Page 1 of 1
APPLICATION NO.  : 10/573054
DATED            : January 21, 2014
INVENTOR(S)      : Liu et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2192 days.

Signed and Sealed this
Twenty-second Day of September, 2015

Michelle K. Lee
*Director of the United States Patent and Trademark Office*